(12) United States Patent
Kahook

(10) Patent No.: US 12,213,920 B2
(45) Date of Patent: *Feb. 4, 2025

(54) INTRAOCULAR DEVICE FOR DUAL INCISIONS

(71) Applicant: THE REGENTS OF THE UNIVERSITY OF COLORADO, Denver, CO (US)

(72) Inventor: Malik Y. Kahook, Denver, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/409,312

(22) Filed: Jan. 10, 2024

(65) Prior Publication Data

US 2024/0148555 A1    May 9, 2024

Related U.S. Application Data

(60) Continuation of application No. 17/994,862, filed on Nov. 28, 2022, now Pat. No. 11,896,530, which is a
(Continued)

(51) Int. Cl.
*A61F 9/013* (2006.01)
*A61B 17/3209* (2006.01)
*A61F 9/007* (2006.01)

(52) U.S. Cl.
CPC ........ *A61F 9/0133* (2013.01); *A61B 17/3209* (2013.01); *A61F 9/00736* (2013.01); *A61F 9/00781* (2013.01)

(58) Field of Classification Search
CPC .. A61F 9/007; A61F 9/00736; A61F 9/00754; A61F 9/00781; A61F 9/013;
(Continued)

(56) References Cited

U.S. PATENT DOCUMENTS 2,130,949 A    9/1938   Campbell
3,776,238 A    12/1973  Peyman
(Continued)

FOREIGN PATENT DOCUMENTS

EP    0073803    7/1985
EP    1455698    9/2004
(Continued)

OTHER PUBLICATIONS

Am. Acad. of Ophthalmology Section 10 Glaucoma, in Basic and Clinical Science Course 2000-2001 (2000), pp. 3-24 and 147-174.
(Continued)

*Primary Examiner* — Todd J Scherbel
(74) *Attorney, Agent, or Firm* — MORGAN, LEWIS & BOCKIUS LLP

(57) ABSTRACT

A microsurgical device and methods of its use can be used for treatment of various conditions including eye diseases, such as glaucoma, using minimally invasive surgical techniques. A device can be used for cutting the trabecular meshwork ("TM") in the eye. The device tip provides entry into the Schlemm's canal via its size (i.e., for example, 0.2-0.3 mm width) and configuration where a ramp elevates the TM away from the outer wall of the Schlemm's canal and guides the TM to first and second lateral elements for creating first and second incisions through the TM. The dimensions and configuration of the device is such that an entire strip of TM is removed without leaving TM leaflets behind and without causing collateral damage to adjacent tissues.

20 Claims, 26 Drawing Sheets

Related U.S. Application Data continuation of application No. 17/402,244, filed on Aug. 13, 2021, now Pat. No. 11,896,529, which is a continuation of application No. 16/997,663, filed on Aug. 19, 2020, now Pat. No. 11,110,008, which is a continuation of application No. 16/678,785, filed on Nov. 8, 2019, now Pat. No. 10,786,391, which is a continuation of application No. 15/701,306, filed on Sep. 11, 2017, now Pat. No. 10,945,885, which is a continuation of application No. 15/484,041, filed on Apr. 10, 2017, now Pat. No. 9,757,279, which is a division of application No. 15/207,329, filed on Jul. 11, 2016, now Pat. No. 9,872,799, which is a continuation-in-part of application No. 14/375,350, filed as application No. PCT/US2013/037374 on Apr. 19, 2013, now Pat. No. 10,327,947.

(60) Provisional application No. 61/637,611, filed on Apr. 24, 2012.

(58) Field of Classification Search
CPC ............. A61F 9/0133; A61F 9/0136; A61F 2009/00868; A61B 17/3209; A61B 17/32093; A61B 17/3211
See application file for complete search history.

(56) References Cited

U.S. PATENT DOCUMENTS

| | | |
|---|---|---|
| 3,882,872 A | 5/1975 | Douvas et al. |
| 4,011,869 A | 3/1977 | Seiler, Jr. |
| 4,111,207 A | 9/1978 | Seiler, Jr. |
| 4,373,530 A | 2/1983 | Kilejian |
| 4,428,748 A | 1/1984 | Peyman et al. |
| 4,501,274 A | 2/1985 | Skjaerpe |
| 4,559,942 A | 12/1985 | Eisenberg |
| 4,577,629 A | 3/1986 | Martinez |
| 4,649,919 A | 3/1987 | Thimsen et al. |
| 4,682,597 A | 7/1987 | Myers |
| 4,900,300 A | 2/1990 | Lee |
| 5,042,008 A | 8/1991 | Iwasa et al. |
| 5,163,433 A | 11/1992 | Kagawa et al. |
| 5,217,476 A | 6/1993 | Wishinsky |
| 5,222,959 A | 6/1993 | Anis |
| 5,224,950 A | 7/1993 | Prywes |
| 5,258,002 A | 11/1993 | Jeffers |
| 5,342,370 A | 8/1994 | Simon et al. |
| 5,364,409 A | 11/1994 | Kuwabara |
| 5,431,671 A | 7/1995 | Nallakrishnan |
| 5,478,338 A | 12/1995 | Reynard |
| 5,487,747 A | 1/1996 | Stagmann et al. |
| 5,536,259 A | 7/1996 | Utterberg |
| 5,558,637 A | 9/1996 | Allonen et al. |
| 5,569,283 A | 10/1996 | Green et al. |
| 5,620,453 A | 4/1997 | Nallakrishnan |
| 5,674,233 A | 10/1997 | Dybbs |
| 5,713,915 A | 2/1998 | Van Heugten et al. |
| 5,817,115 A | 10/1998 | Nigam |
| 5,865,831 A | 2/1999 | Cozean et al. |
| 6,013,049 A | 1/2000 | Rockley et al. |
| 6,139,559 A | 10/2000 | Nordan et al. |
| 6,213,997 B1 | 4/2001 | Hood et al. |
| 6,241,721 B1 | 6/2001 | Cozean et al. |
| 6,251,103 B1 | 6/2001 | Berlin |
| 6,264,668 B1 | 7/2001 | Prywes |
| 6,358,262 B1 | 3/2002 | Chan et al. |
| 6,388,043 B1 | 5/2002 | Langer et al. |
| 6,428,501 B1 | 8/2002 | Reynard |
| 6,497,712 B1 | 12/2002 | Feaster |
| 6,503,262 B1 | 1/2003 | Edens |
| 6,720,402 B2 | 4/2004 | Langer et al. |
| 6,759,481 B2 | 7/2004 | Tong |
| 6,979,328 B2 | 12/2005 | Baerveldt et al. |
| 7,374,566 B1 | 5/2008 | Schossau |
| 7,604,663 B1 | 10/2009 | Reimink et al. |
| 7,632,303 B1 | 12/2009 | Stalker et al. |
| 7,648,591 B2 | 1/2010 | Furst et al. |
| 7,785,321 B2 | 8/2010 | Baerveldt et al. |
| 7,883,519 B2 | 2/2011 | Oren |
| 7,935,131 B2 | 5/2011 | Anthamatten et al. |
| 7,955,387 B2 | 6/2011 | Richter |
| 7,959,641 B2 | 6/2011 | Sorensen et al. |
| 8,038,923 B2 | 10/2011 | Berger et al. |
| 9,107,729 B2 | 8/2015 | Sorensen et al. |
| 9,757,279 B2 | 9/2017 | Kahook |
| 9,872,799 B2 | 1/2018 | Kahook |
| 10,327,947 B2 | 6/2019 | Kahook |
| 10,786,391 B2 | 9/2020 | Kahook |
| 10,945,885 B2 | 3/2021 | Kahook |
| 11,896,530 B2 * | 2/2024 | Kahook ............ A61F 9/0133 |
| 2001/0029386 A1 | 10/2001 | Matsutani et al. |
| 2002/0026205 A1 | 2/2002 | Matsutani et al. |
| 2002/0111608 A1 | 8/2002 | Baerveldt et al. |
| 2003/0208217 A1 | 11/2003 | Dan |
| 2005/0015104 A1 | 1/2005 | Morawski |
| 2005/0070941 A1 | 3/2005 | Isogimi |
| 2005/0113644 A1 | 5/2005 | Obenchain et al. |
| 2005/0216019 A1 | 9/2005 | Eckman |
| 2005/0245953 A1 | 11/2005 | Cote |
| 2006/0015128 A1 | 1/2006 | Fard |
| 2006/0106370 A1 | 5/2006 | Baerveldt et al. |
| 2006/0149194 A1 | 7/2006 | Conston et al. |
| 2006/0241580 A1 | 10/2006 | Mittelstein et al. |
| 2006/0271074 A1 | 11/2006 | Ewers et al. |
| 2007/0073275 A1 | 3/2007 | Conston et al. |
| 2007/0100363 A1 | 5/2007 | Dollar et al. |
| 2007/0276420 A1 | 11/2007 | Sorensen et al. |
| 2009/0248141 A1 | 10/2009 | Shandas et al. |
| 2009/0287233 A1 | 11/2009 | Huculak |
| 2009/0306689 A1 | 12/2009 | Welty et al. |
| 2010/0152609 A1 | 6/2010 | Zwolinksi et al. |
| 2010/0268175 A1 | 10/2010 | Lunsford |
| 2011/0077626 A1 | 3/2011 | Baerveldt et al. |
| 2011/0202049 A1 | 8/2011 | Jia et al. |
| 2011/0230877 A1 | 9/2011 | Huculak |
| 2012/0083727 A1 | 4/2012 | Barnett |
| 2012/0116437 A1 | 5/2012 | Hörauf |
| 2012/0239056 A1 | 9/2012 | Dijkman et al. |
| 2014/0030273 A1 | 1/2014 | Verploegen et al. |
| 2014/0121697 A1 | 5/2014 | Scheller et al. |
| 2015/0045820 A1 | 2/2015 | Kahook |
| 2016/0354248 A1 | 12/2016 | Kahook |
| 2017/0181892 A1 | 6/2017 | Kahook et al. |
| 2017/0367890 A1 | 12/2017 | Kahook |
| 2018/0133056 A1 | 5/2018 | Kahook |

FOREIGN PATENT DOCUMENTS

| | | |
|---|---|---|
| EP | 1615604 | 1/2006 |
| EP | 2303203 | 4/2011 |
| JP | H09276284 A | 10/1997 |
| JP | 2005103035 A | 4/2005 |
| JP | 2010099388 A | 5/2010 |
| JP | 2012531983 A | 12/2012 |
| JP | 2015516214 A | 6/2015 |
| JP | 2019500989 A | 1/2019 |
| KR | 1020040058309 | 9/2004 |
| WO | WO-9306800 | 4/1993 |
| WO | WO-2001078631 | 10/2001 |
| WO | WO-2003045290 | 6/2003 |
| WO | WO-2004093761 | 11/2004 |
| WO | WO-2004110501 | 12/2004 |
| WO | WO-2009140185 | 11/2009 |
| WO | WO-2011030081 | 3/2011 |
| WO | WO-2012044952 | 4/2012 |
| WO | WO-2012137186 | 10/2012 |

(56) References Cited

FOREIGN PATENT DOCUMENTS

| WO | WO-2013163034 | 10/2013 |
|----|----|----|
| WO | WO-2017112893 | 6/2017 |

OTHER PUBLICATIONS

Am. Acad. of Ophthalmology, Section 8 External Disease and Cornea, in Basic and Clinical Science Course 2001-2002 (2001), pp. 437-442.

Anderson, "Trabeculotomy compared to goniotomy for glaucoma in children," Ophthalmology, 1983, 90(7), pp. 805-806.

Barkan, O., "Goniotomy for the Relief of Congenital Glaucoma", Br J Ophthalmol. Sep. 1948; 32(9):701-708.

Dominguez, A., "Trabéculectomie Ab Interno", Bulletins et mémoires de la Société française d'ophtalmologie, 86(0):100-105 (1973).

Ellingsen, Bruce A. et al., "Trabeculotomy and sinusotomy in enucleated human eyes", Investigative Ophthalmology & Visual Science Jan. 1972, vol. 11, Issue 1, pp. 21-28, downloaded from iovs.arvojournals.org on Feb. 23, 2019.

European Office Action for Application No. 13781487.7, dated Dec. 20, 2018, 4 pages.

Extended European Search Report and Written Opinion for Application No. 16880112.4, dated Aug. 2, 2019, 6 pages.

File History for U.S. Appl. No. 13/159,356.

File History for U.S. Pat. No. 9,107,729.

Francis et al., "Ab interno trabeculectomy: development of a novel device (Trabectome®) and surgery for open-angle glaucoma," Journal of Glaucoma, 2006, 15(1), pp. 68-73.

Grant, "Clinical measurements of aqueous outflow," AMA Archives of Ophthalmology, 1951, 46(2), pp. 113-131.

Grant, "Experimental aqueous perfusion in enucleated human eyes," Archives of Ophthalmology, 1963, 69(6), pp. 783-801.

Grant, Morton W., "Symposium: Microsurgery of the Outflow Channels", Trans Am Acad Ophthalmol Otolaryngol. Mar.-Apr. 1972;76(2):398-404.

Herschler et al., "Modified goniotomy for inflammatory glaucoma. Histologic evidence for the mechanism of pressure reduction," Archives of Ophthalmology, 1980, 98(4), pp. 684-687.

Hogan, M. J., "History of the Human Eye: an Atlas and Textbook", Philadelphia, Pennsylvania: W. B. Saunders Company (1971), p. 135.

International Search Report and Written Opinion for Application No. PCT/US2016/068393, dated Apr. 17, 2017, 29 pages.

International Search Report and Written Opinion for Application No. PCT/US2018/056935, dated Jan. 31, 2019, 12 pages.

Jacobi et al., "Goniocurettage for removing trabecular meshwork: clinical results of a new surgical technique in advanced chronic open-angle glaucoma," American Journal of Ophthalmology, 1999, 125(5), pp. 505-510.

Jacobi et al., "Technique of goniocurettage: a potential treatment for advanced chronic open angle glaucoma," British Journal of Ophthalmology, 1997, 81(4) pp. 302-307.

Jacobi, P. C et al., "Perspectives in trabecular surgery", Eye 2000;14(Pt 3B)(3b):519-530 (2000).

Japanese Office Action for Application No. 2020-522359, dated Mar. 29, 2023, 6 pages including translation.

Japanese Office Action for Application No. 2020-522359, dated Sep. 2, 2022, 6 pages including translation.

Jea et al., "Ab Interno Trabeculectomy Versus Trabeculectomy for Open-Angle Glaucoma," Ophthalmology, 2012, 119(1), pp. 36-42.

Johnson et al., "Human trabecular meshwork organ culture. A new method," Investigative Ophthalmology & Visual Science, 1987, 26(6), pp. 945-953.

Latimer, K. et al., "Insight Into Glaucoma Treatment in the Early 1900s: Harvey Cushing's 1905 Operation", Arch Ophthalmol. 2012;130(4):510-513 (Apr. 2012).

Luntz et al., "Trabeculotomy ab externo and trabeculectomy in congenital and adult-onset glaucoma," American Journal of Ophthalmology, 1977, 83(2), pp. 174-179.

M. Johnstone et al., "Microsurgery of Schlemm's Canal and the Human Aqueous Outflow System," Am. J. Ophthalmology 76(6):906-917 (1973) ("Johnstone 1973").

Manuel Quintana, Gonioscopic Trabeculotomy. First Results, in 43 Second European Glaucoma Symposium, Documenta Ophthalmologica Proceedings Series 265 (E.L. Greve, W. Leydhecker, & C. Raitta ed., 1985) ("Quintana 1985").

Minckler et al., "Clinical Results with the Trabectome® for Treatment of Open-Angle Glaucoma," Ophthalmology, 2005, 112(6), pp. 962-967.

Pantcheva et al., "Ab Interno Trabeculectomy," Middle East African Journal of Ophthalmology, 2010, 17(4), pp. 287-289.

Patent Owner's Mandatory Notices in PTAB Case No. PGR2021-00026 related to U.S. Pat. No. 10,786,391, dated Jan. 7, 2021, 5 pages.

PCT International Search Report of International Application No. PCT/US2013/037374 dated Jul. 25, 2013.

Petition for Post-Grant Review of U.S. Pat. No. 10,786,391, dated Dec. 17, 2020, 82 pages.

Quigley et al., "The numbeer of people with glaucoma worldwide in 2010 and 2020," British Journal of Ophthalmology, 2006, 90(3), pp. 262-267.

Seibold et al., "Preclinical Investigation of Ab Interno Trabeculectomy Using a Novel Dual-Blade Device," American Journal of Ophthalmology, 2013, 155(3), pp. 524-529.e522.

Shields, M. B., Textbook of Glaucoma, Fourth Edition. Baltimore, Maryland: Williams & Wilkins (1998), pp. 1-31, 351-352, 456-460, and 470-489.

Supplementary European Search Report for Application No. 13781487.7, mailed Jul. 9, 2015, 7 pages.

Tan et al., "Postoperative complications after glaucoma surgery for primary angle-closure glaucoma vs primary open-angle glaucoma," Archives of Ophthalmology, 2011, 129(8), pp. 987-992.

Ting et al., "Ab interno trabeculectomy: Outcomes in exfoliation versus primary open-angle glaucoma," Journal of Cataract & Refractive Surgery, 2012, 38(2), pp. 315-313.

U.S. Office Action for U.S. Appl. No. 15/701,306, dated May 18, 2020, 11 pages.

Japanese Office Action for Application No. 2022-533358, dated Jul. 23, 2024, 4 pages including translation.

Extended European Search Report for Application No. 24194482.6, dated Nov. 14, 2024, 9 pages.

Japanese Office Action for Application No. 2023-191980, dated Oct. 2, 2024, 10 pages inlcuding translation.

\* cited by examiner

DETAIL D

INTRAOCULAR DEVICE FOR DUAL INCISIONS

RELATED APPLICATIONS

The present application is a continuation of U.S. patent application Ser. No. 17/994,862 filed on Nov. 28, 2022, now U.S. Pat. No. 11,896,530, issued on Feb. 13, 2024, which is a continuation of U.S. patent application Ser. No. 17/402,244 filed on Aug. 13, 2021, which is a continuation of U.S. patent application Ser. No. 16/997,663 filed on Aug. 19, 2020, now U.S. Pat. No. 11,110,008, issued on Sep. 7, 2021, which is a continuation of U.S. patent application Ser. No. 16/678,785 filed on Nov. 8, 2019, now U.S. Pat. No. 10,786,391, issued on Sep. 29, 2020, which is a continuation of U.S. patent application Ser. No. 15/701,306 filed on Sep. 11, 2017, now U.S. Pat. No. 10,945,885, issued on Mar. 16, 2021, which is a continuation of U.S. patent application Ser. No. 15/484,041 filed on Apr. 10, 2017, now U.S. Pat. No. 9,757,279, issued on Sep. 12, 2017, which is a divisional of U.S. patent application Ser. No. 15/207,329 filed on Jul. 11, 2016, now U.S. Pat. No. 9,872,799, issued on Jan. 23, 2018, which is a continuation-in-part of U.S. patent application Ser. No. 14/375,350 filed on Jul. 29, 2014, now U.S. Pat. No. 10,327,947, issued on Jun. 25, 2019, which is a national stage entry of PCT Application No. PCT/US2013/037374 filed on Apr. 19, 2013, which claims the benefit of U.S. Provisional Patent Application No. 61/637,611 filed on Apr. 24, 2012, each of which is incorporated herein by reference in its entirety.

BACKGROUND

There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel, cutting blade or needle) in the eye, skin, mucous membrane, tumor, organ or other tissue or a human or animal. In addition, it may sometimes be desirable to remove a strip or quantity of tissue from the body of a human or animal for use as a biopsy specimen, for chemical/biological analysis, for retention or archival of DNA identification purposes, etc. In addition, some surgical procedures require removal of a strip of tissue of a known width from an anatomical location within the body of a patient.

One surgical procedure wherein a strip of tissue of a known width is removed from an anatomical location within the body of a patient is an ophthalmological procedure used to treat glaucoma. This ophthalmological procedure is sometimes referred to as a goniotomy. In a goniotomy procedure, a device that is operative to cut or ablate a strip of tissue of approximately 2-10 mm in length or more and about 50-230 µm in width is inserted into the anterior chamber of the eye and used to remove a full thickness strip of tissue from the trabecular meshwork. The trabecular meshwork is a loosely organized, porous network of tissue that overlies a collecting canal known as Schlemm's canal. A fluid, known as aqueous humor, is continually produced in the anterior chamber of the eye. In healthy individuals, aqueous humor flows through the trabecular meshwork, into Schlemm's canal and out of the eye through a series of ducts called collector channels. In patients who suffer from glaucoma, the drainage of aqueous humor from the eye may be impaired by elevated flow resistance through the trabecular meshwork, thereby resulting in an Increase in intraocular pressure. The goniotomy procedure can restore normal drainage of aqueous humor from the eye by removing a full thickness segment of the trabecular meshwork, thus allowing the aqueous humor to drain through the open area from which the strip of trabecular meshwork has been removed.

SUMMARY

Embodiments of the present disclosure can be used for surgical medicinal intervention. For example, some embodiments relate to a microsurgical device and methods of its use for treatment of various medical conditions including but not limited to eye diseases, such as glaucoma, using minimally invasive surgical techniques. Specifically, the device may be a dual-blade device for cutting the trabecular meshwork ("TM") in the eye. In particular, the device may have a device tip providing entry into the Schlemm's canal via its size (i.e., for example, between approximately 0.2-0.3 mm width) and a configuration where the entry blade tip ramps upwardly providing a wedge or ramp-like action for cutting the TM.

To facilitate the understanding of the present disclosure, a number of terms are defined below.

Terms defined herein have meanings as commonly understood by a person of ordinary skill in the areas relevant to the present disclosure. Terms such as "a," "an," and "the" are not intended to refer to only a singular entity, but include the general class of which a specific example may be used for illustration.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "therapeutically effective amounts" or "pharmaceutically effective amounts", as used herein means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, embodiments of the present disclosure also contemplate treatment that merely reduces symptoms, improves (to some degree) and/or delays disease progression. It is not intended that embodiments of the present disclosure be limited to instances wherein a disease or affliction is cured. It is sufficient that symptoms are reduced.

As used herein "goniotomy" refers to a surgical procedure primarily used to treat various types of glaucoma (ex, primary open angle glaucoma).

As used herein "trabecular meshwork" refers to area of tissue in the eye located around the base of the cornea, near the ciliary body, (between the scleral spur and Schwalbe's line) and is responsible for draining the aqueous humor from the eye via the anterior chamber (the chamber on the front of the eye covered by the cornea). The tissue is spongy and lined by trabeculocytes; it allows fluid to drain into a circular channel in the eye called Schlemm's canal and eventually flowing into the blood system.

As used herein "Schlemm's canal" refers to a circular channel in the eye that collects aqueous humor from the anterior chamber and delivers it into the bloodstream via the collector channels and anterior ciliary veins.

As used herein "eye diseases" refers to various conditions of the eye including, but not limited to Glaucoma—optic neuropathy, Glaucoma suspect—ocular hypertension, Primary open-angle glaucoma, Primary angle-closure glaucoma, primary open angle glaucoma, normal or low tension glaucoma, pseudoexfoliation glaucoma, pigment dispersion glaucoma, angle closure glaucoma (acute, subacute, chronic), neovascular or inflammatory glaucoma, ocular hypertension, and other types of glaucoma that are related to dysregulation of intraocular pressure.

As used herein "hypotony" refers to reduced intraocular pressure. The statistical definition of hypotony is intraocular pressure ("IOP") less than 6.5 mmHg, which is more than 3 standard deviations below the mean IOP. The clinical definition of hypotony is IOP low enough to result in pathology (vision loss). The vision loss from low IOP may be caused by corneal edema, astigmatism, cystoid macular edema, maculopathy, or other condition. Hypotony maculopathy is characterized by a low IOP associated with fundus abnormalities, including chorioretinal folds, optic nerve head edema in the acute setting, and vascular tortuosity.

As used herein "Schwalbe's line" refers to the anatomical line found on the interior surface of the eye's cornea, and delineates the outer limit of the corneal endothelium layer. Specifically, it represents the termination of Descemet's membrane.

As used herein "Descemet's membrane" refers to the basement membrane that lies between the corneal proper substance, also called stroma, and the endothelial layer of the cornea.

As used herein "scleral spur" refers to an annular structure composed of collagen in the human eye, a protrusion of the sclera into the anterior chamber. It is the origin of the longitudinal fibers of the ciliary muscle and is attached anteriorly to the trabecular meshwork. Open-angle glaucoma (OAG) and closed-angle glaucoma (CAG) may be treated by muscarinic receptor agonists (e.g., pilocarpine), which cause rapid miosis and contraction of the ciliary muscles, this pulls the scleral spur and results in the trabecular meshwork being stretched and separated. This opens the fluid pathways and facilitates drainage of the aqueous humour into the canal of Schlemm and ultimately decreasing intraocular pressure.

As used herein "Trabectome®" refers to a minimally invasive glaucoma surgical electrosurgical or ablation tool for the surgical management of adult, juvenile and infantile glaucoma. Unlike a trabeculectomy, the surgery with a Trabectome® should not create an external filtering bleb or require leaving a permanent hole in the eye. Instead, the Trabectome® electro-surgical handpiece opens access to the eyes natural drainage system.

Embodiments of the present disclosure are illustrated, for example, according to various aspects described below.

According to some embodiments, disclosed is a device for severing a trabecular meshwork, comprising: a handle; a shaft extending along a longitudinal axis; a platform extending from the shaft for elevating a portion of the trabecular meshwork away from an outer wall of Schlemm's canal, the platform comprising: a tip at a distal side of the platform configured to pierce the trabecular meshwork; a bottom surface; a planar ramp extending from the distal side to a proximal side of the platform opposite the distal side; first and second angled sides extending from the bottom surface to the planar ramp and from the tip toward the proximal side of the platform, wherein a width between the first and second angled sides increases toward the proximal side of the platform; and first and second lateral sides laterally distal from the shaft and having a height greater than the first and second angled sides, wherein a portion of the first lateral side defines a first lateral element and a portion of the second lateral side defines a second lateral element; wherein when the planar ramp is advanced between the trabecular meshwork and an outer wall of the Schlemm's canal, a portion of the trabecular meshwork on the planar ramp is elevated away from the outer wall of the Schlemm's canal without cutting the portion of the trabecular meshwork from surrounding portions of the trabecular meshwork and the portion is guided to the first and second lateral elements; and wherein portions of the first and second lateral sides are configured to sever trabecular meshwork tissue as the trabecular meshwork tissue advances in a rearward direction over the platform.

According to some embodiments, disclosed is a device for severing a trabecular meshwork, comprising: a handle; a shaft extending along a longitudinal axis; a platform extending from the shaft for elevating a portion of the trabecular meshwork away from an outer wall of Schlemm's canal, the platform comprising: a tip at a distal side of the platform configured to pierce the trabecular meshwork; a bottom surface; a planar ramp extending from the distal side to a proximal side of the platform opposite the distal side; a right edge and a left edge extending towards the distal side of the platform from the tip, where the right edge and the left edge have a first height at the tip and a second height near the distal side of the platform, the second height being greater than the first height; wherein when the planar ramp is advanced between the trabecular meshwork and the outer wall of Schlemm's canal, a portion of the trabecular meshwork on the planar ramp is elevated away from the outer wall of the Schlemm's canal without cutting the portion of the trabecular meshwork from surrounding portions of the trabecular meshwork and the portion of the trabecular meshwork is guided to the right and left edges; and wherein portions of the right and left edges are configured to sever trabecular meshwork tissue as the trabecular meshwork tissue advances in a rearward direction over the platform.

Creating the first and second incisions can comprise creating only the first and second incisions. The strip between the first and second incisions remains intact after creating the first and second incisions. The method can further comprise excising the strip from the trabecular meshwork after the strip has reached a desired length. The excising can be performed with forceps. Creating the first and second incisions can be performed without ablation or burning of the trabecular meshwork. Creating the first and second incisions can be performed while the portion of the trabecular meshwork is stretched to be elevated away from the outer wall of the Schlemm's canal. Creating the first and second incisions can be performed while the portion of the trabecular meshwork is under tension that is greater than the tension of the trabecular meshwork in a natural state. The method can further comprise, while creating the first and second incisions, a portion of the strip is received within the gap. The first lateral element can create the first incision along a first portion of the trabecular meshwork that is guided along a first side of the platform, and the second lateral element can create the second incision along a second portion of the trabecular meshwork that is guided along a second side of the platform.

Creating the first and second incisions comprises creating only the first and second incisions. The strip between the first and second incisions can remain intact after creating the first and second incisions. The method can further comprise excising the strip from the trabecular meshwork after the strip has reached a desired length. The excising can be performed with forceps. Creating the first and second incisions can be performed without cautery or burning of the trabecular meshwork. Creating the first and second incisions can be performed while the portion of the trabecular meshwork is stretched to be elevated away from the outer wall of the Schlemm's canal. Creating the first and second incisions can be performed while the portion of the trabecular meshwork is under tension that is greater than the tension of the trabecular meshwork in a natural state. The method can further comprise, while creating the first and second incisions, a portion of the strip is received within the gap. The first lateral element can create the first incision along a first portion of the trabecular meshwork that is guided along a first side of the platform, and the second lateral element can create the second incision along a second portion of the trabecular meshwork that is guided along a second side of the platform.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 20 shows damage to sclera below Schlemm's canal by the blade.

FIG. 21 shows thermal damage to the TM. For the Trabectome® procedure (designed to replace goniotomy and to improve upon that procedure by removing sections of trabecular meshwork) a Trabectome® device was used to engage the trabecular meshwork and cautery was applied to the trabecular meshwork. The circle shows an area where a small segment of trabecular meshwork was removed; however, there are large leaflets of trabecular meshwork remaining and charred tissue on either side of the treatment area. In this previous methodology, the device "burns" tissue and the burning of tissue creates inflammation that leads to more scar formation that leads to failure of the surgically induced opening into Schlemm's canal. In addition, due to ablation, many bubbles are formed during this procedure, which makes visualization difficult during the actual procedure. These issues do not occur with embodiments of the present disclosure. A representative photo of the Trabectome® is in FIG. 21

FIG. 22 shows no damage to structures adjacent to the normal location of TM. FIG. 22 shows complete removal of TM tissue with no remaining leaflets of TM.

DETAILED DESCRIPTION

Figure 1:
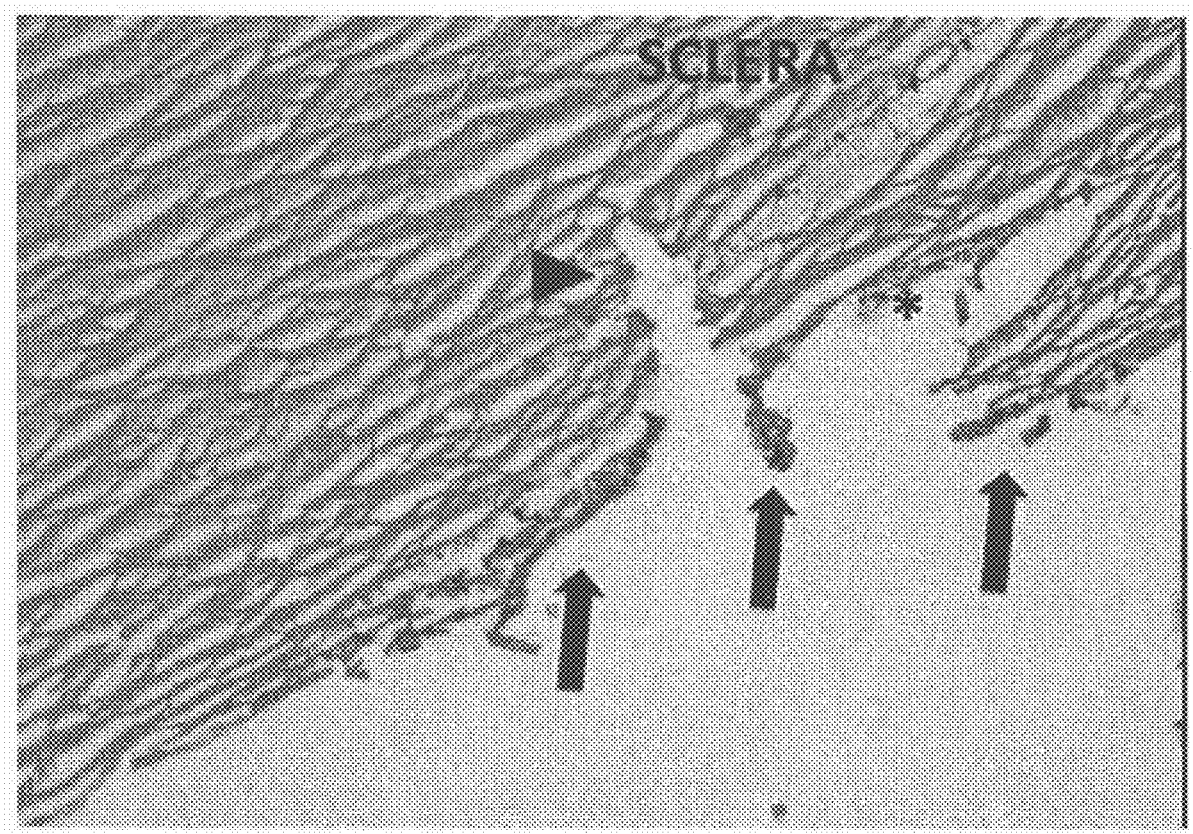
FIG. 1 shows a representative histologic specimen of human anterior chamber angle structures following incision with a microvitreoretinal ("MVR") blade. The incision extends through full-thickness trabecular meshwork and the Schlemm's canal and into adjacent sclera (black arrow head). A large portion of trabecular meshwork remains on either side of the incision (black arrows). An asterisk labels the Schlemm's canal. Light micrograph, hematoxylin-eosin, magnification ×100.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

There are several practical advantages of a dual blade device, as contemplated herein, for use in goniotomy. First, a dual blade device may be reusable and can be added to a standard cataract surgical tray. Second, the lack of moving parts or the need for coupled irrigation or a separate power source allows for inexpensive manufacturing and rapid acquisition of surgical expertise. This would permit easy, economical access to a new technique, especially in underserved locations around the world. The simple design and material requirements of dual-blade device embodiments would be more economical. Finally, in contrast to other techniques for TM removal, embodiments of dual-blade device designs conform to the Schlemm's canal anatomy, minimize damage to adjacent tissues, and provide excellent control over excised tissue. Therefore, the presented dual-blade minimally invasive glaucoma surgery ("MIGS") device represents a novel technique to perform a goniotomy with or without concomitant cataract extraction. In some embodiments, the dual-blade devices are capable of a more complete removal of TM tissue from the anterior chamber angle in a simple and inexpensive manner as compared to conventional devices. Perfusion eye studies support the potential for significant IOP reduction with this technique.

Glaucoma is believed to be one of the leading causes of blindness worldwide. It has been reported that a modifiable disease risk factor is intraocular pressure ("IOP"). Conventional treatment has centered on lowering IOP pharmaceutically with hypotensive medications or surgically through the use of lasers or incisional procedures. The main area of obstruction to aqueous outflow, with subsequent dysregulation of IOP, is thought to be located at the juxtacanalicular trabecular meshwork ("TM") and distal outflow structures. Performing a goniotomy or trabeculotomy in adults with glaucoma has not been associated with great success in lowering IOP. In contrast, these procedures have been reported to be more successful in congenital glaucoma, where a membrane covering the TM is thought to be a major factor in impedance of aqueous outflow. More recently, there have been attempts to use ab interno trabeculectomy procedures to remove TM in adult patients and results have been mixed.

One reason for poor long-term outcomes with this approach in adults might be related to incomplete removal of TM and membrane formation across the remaining TM leaflets with subsequent elevation in IOP. It is unclear how a more complete removal of TM tissue might compare to procedures that simply incise TM, such as a single incision goniotomy, or procedures that cauterize TM with tissue removal, such as Trabectome® (Neomedix, Tustin, California, USA). The dual-blade device is specifically designed to conform to the drainage angle anatomy of the human eye. The device can be used to perform a dual incision goniotomy by engaging TM and cutting the target tissue while minimizing leaflets left in place and damage to adjacent tissues. The device was designed and manufactured at the University of Colorado Eye Center. Tissue effects from the device are compared to those from a single incision goniotomy using a microvitreoretinal ("MVR") blade (BD, Franklin Lakes, New Jersey, USA) and cautery of TM with the Trabectome® device. Human eye perfusion studies were also completed to assess the IOP-lowering efficacy of each approach.

Recently, there has been a growing trend toward innovations in MIGS. The risks and imperfections of guarded filtration surgery and tube shunt procedures have driven this paradigm shift despite the proven long-term efficacy of these incisional procedures. Drawbacks of traditional incisional procedures include unpredictable IOP-lowering results, prolonged visual recovery, long-term risk of infection and vision loss, frequency of follow-up visits, and long-term failure rate. Procedures such as endoscopic cyclophotocoagulation, ab interno trabeculectomy with Trabectome®, and canaloplasty with the iScience illuminated catheter (iScience, Menlo Park, California, USA) were all introduced to address limitations of full-thickness surgery, most notably to eliminate the presence of a filtering bleb. However, a major drawback of all of these procedures is the additional equipment cost required and, in some cases, a steep learning curve. The added equipment cost in particular presents a significant hurdle to providers, hospitals, and surgery centers that may require several procedures to recoup the initial investment. Providers and patients may also face opposition from insurance companies regarding coverage of a procedure lacking long-term efficacy data. The requirement for additional equipment also limits patient access to these procedures in underserved areas of the world.

A goniotomy is generally referred to as a surgical procedure used to treat glaucoma. Glaucoma can be caused by blockage in the trabecular meshwork and/or a developmental arrest of some of the structures within the anterior (front) segment of the eye. These changes lead to an excess of fluid in the eye, which can cause pressure that can damage the internal structures of the eye leading to optic neuropathy and loss of vision.

One type of glaucoma that can be treated with goniotomy is known as congenital glaucoma. Congenital glaucoma is caused by a decrease in or even a complete obstruction of the outflow of intraocular fluid. The ocular syndromes and anomalies that predispose a child to congenital glaucoma include the following: Reiger's anomaly; Peter's anomaly; Axenfeld's syndrome; and Axenfeld-Rieger's syndrome. Systemic disorders that affect the eyes in ways that may lead to glaucoma include Marian's syndrome; rubella (German measles); and the phacomatoses, which include neurofibromatosis and Sturge-Weber syndrome. Since these disorders affect the entire body as well as the eyes, the child's pediatrician or family doctor will help to diagnose and treat these diseases.

One purpose of a goniotomy is to clear the obstruction to aqueous outflow from the eye, which in turn lowers the intraocular pressure ("IOP"). This is a treatment method for any type of glaucoma including primary open angle glaucoma and chronic angle closure glaucoma.

Before the surgeon begins the procedure, the patient may be given miotics, which are drugs that cause the pupil to contract. The partial closure may improve the surgeon's view of and access to the trabecular meshwork; it may also protect the lens of the eye from trauma during surgery. Other drugs may be administered to lower the intraocular pressure. Goniotomy procedures may be done without use of miotics. In some embodiments, devices may be used in the setting of a dilated (non-miotic) pupil, as can devices described as prior art.

Once the necessary drugs have been given and the patient is anesthetized, the surgeon may use forceps or sutures to stabilize the eye in the correct position. The patient's head may be rotated away from the surgeon so that the interior structures of the eye are more easily seen. Next, with either a knife-needle or a goniotomy knife, the surgeon punctures the cornea while looking at the interior of the eye through a microscope or a loupe. An assistant may use a syringe to introduce fluid into the eye's anterior chamber through a viscoelastic tube as the surgeon performs the goniotomy.

A gonioscopy lens may be then placed on the eye. As the eye is rotated by an assistant, the surgeon sweeps the knife blade or needle through 90-120 degrees of arc in the eye, making incisions in the anterior trabecular meshwork, avoiding the posterior part of the trabecular meshwork in order to decrease the risk of damage to the iris and lens. Endoscopic visualization may also be used to guide cutting. In some embodiments, devices may be placed at the end of an endoscope, precluding the need for a gonio lens during treatment.

Once the knife and tubing are removed, saline solution may be introduced through the hole to maintain the integrity of the eye and the hole is closed with sutures. The surgeon then applies antibiotics and corticosteroids to the eye to prevent infection and reduce inflammation. The head may be then rotated away from the incision site so that blood cannot accumulate. The second eye may be operated on at the same time. If the procedure needs to be repeated, another area of the eye may be treated.

At present there remains a need in the art for the development of simple, inexpensive and accurate instruments useable to perform the procedure of cutting the TM in the eye and effectively remove a complete full thickness strip of TM without leaving TM leaflets as well as other procedures where it is desired to remove a strip of tissue from a larger mass of tissue.

A goniotomy is simply an incision of the TM to cut it into two leaflets, it is the basic form of cutting TM that all other devices are trying to improve upon. Since it is just an incision, it leaves the entire tissue behind (albeit segmented) and then the tissue scars down and the eye pressure goes up anyway. This may be why "newer" devices are trying to cut and remove the actual TM from the area over Schlemm's canal. The complete removal of TM without leaving leaflets is one key feature differentiating embodiments of the present disclosure from conventional blade goniotomy (e.g., using an MVR blade). The anatomical design of the device of the present disclosure may be better suited for effective removal of complete strips of tissue, in particular the TM, with minimal to no traumatic impact on the surrounding tissue.

Specific advantages of some embodiments described herein as compared to other conventional devices include but are not limited to:
 1. No mechanically moving parts
 2. No cautery or burning of tissue
 3. Two blades are in place on the sides of the device that cut the trabecular meshwork (TM) in a precise fashion leaving little TM behind (current devices leave a lot of TM behind that then scars over)

4. The entry into Schlemm's canal is done with use of the blade tip similar to what has been described for decades in standard goniotomy. Other devices use a non-blade footplate to enter Schlemm's canal.
5. The dimensions of the device allow for complete cutting and fit in Schlemm's canal with precision.
6. The tip of the blade ramps up to the two side blades to present the TM to the two slide blades, which then allows for more precise cutting.
7. The sides of the ramp are devoid of blades or cutting features until the point where the dual blades are present.
8. Cutting of the TM with the dual blades occurs at points elevated from the natural resting position of the TM.

In some embodiments, a device comprises: a handle 1, interface of tool shaft and handle 2, a tool shaft 3, interface of tool shaft and beveled platform 4, beveled platform 5, a first end/beveled platform tip/insertion blade tip 6, a second end/back of the beveled platform 7, a first side 8, a second side 9, a first blade 10, and a second blade 11.

In some embodiments, a device 12 comprises: a handle 1 that necks down to a tool shaft 3 by a first interface 2 wherein said tool shaft widens into a beveled platform 5 by a second interface 4, wherein said beveled platform 5 comprises a insertion blade tip 6 on a distal end of the beveled platform 5 comprising a ramp 13 from said insertion blade tip back towards the posterior end the beveled platform 5, and a first lateral element (e.g., blade) 10 and second lateral element (e.g., blade) 11 along the sides of said beveled platform 5. In some embodiments, said sides of said beveled platform 5 comprise a first side 8 and a second side 9. In some embodiments, the platform 5 includes a first side 8 extending from the proximal side of the platform 5 to the distal side of the platform 5 and a second side 9 extending from the proximal side of the platform 5 to the distal side of the platform 5. In some embodiments, the first side 8 and the second side 9 each form a bevel of the platform 5. In some embodiments, the first side 8 and the second side 9 each form a convex portion of the platform 5. In some embodiments, proximal segments of the first side 8 and the second side 9 are parallel to each other and distal segments of the first side 8 and the second side 9 intersect at the tip 6. In some embodiments, the first lateral element extends from the first side and the second lateral element extends from the second side.

In some embodiments, said first lateral blade 10 and second lateral blade 11 are in a perpendicular alignment to the bottom of the beveled platform. In some embodiments, the first and second lateral blades 10, 11 are straight. In some embodiments, the first and second lateral blades 10, 11 are parallel to each other.

In some embodiments, the ramp 13 increases from a distal width at the distal side (e.g., at the tip 6) to a proximal width, greater than the distal width, at the proximal side (e.g., adjacent to the lateral blades 10, 11). The ramp 13 can be planar, concave, and/or convex. Where the ramp 13 is planar, it can provide a gradual stretching of TM that is elevated by the platform 5 and across the ramp 13. In some embodiments, a maximum width across the first and second lateral elements is not less than a maximum width across the ramp. This allows the incisions to be made at the outer peripheries of the platform, where the first side 8 and the second side 9 elevate and present the TM to the lateral blades 10, 11.

In some embodiments, the device 12 includes a bottom surface 15 that is configured to abut the outer wall of the Schlemm's canal 22 during a procedure. The bottom surface 15 can be planar, convex, concave, or combinations thereof. For example, the bottom surface 15 can include a concave portion between at least two lateral edges. For example, lateral edges can be provided below the first side 8 and the second side 9 of the ramp 13, with a concave portion formed between the lateral edges. The lateral edges can make contact with the outer wall of the Schlemm's canal 22 during a procedure.

In some embodiments, a device 12 comprises a handle 1 and a beveled platform 5, wherein said platform 5 is set at a specific angle and orientation relative to said handle 1. In some embodiments, a device 12 comprises a handle 1 and a beveled platform 5, wherein said platform 5 freely rotates in at least two dimensions. In some embodiments, said handle 1 and beveled platform 5 are operably attached at an angle ranging between 90 and 120 degrees in the Y-Z axis (shown in FIG. 15). In some embodiments, said handle 1 and beveled platform 5 are operably attached at an angle ranging between 90 and 180 degrees in the X-Z axis (shown in FIG. 10). In some embodiments, said platform 5 freely rotates in an X-Y dimension relative to said handle 1. In some embodiments, said platform 5 remains at a fixed angle in the X-Y, X-Z, and Y-Z dimensions relative to said handle 1 (shown in FIG. 15). In some embodiments, said platform 5 freely rotates in a positive Z dimension relative to said handle 1.

In some embodiments, said beveled platform 5 comprises a first end/beveled platform tip/insertion blade tip 6 and a second end/back of the beveled platform 7, wherein said second end/back of the beveled platform 7 is between 2 and 30 times greater in thickness relative to said first end/beveled platform tip/insertion blade tip 6. The thickness can be measured along the Z-axis, such as through a surface of the ramp 13 and the base of the platform 5. In some embodiments, the dimensions of the beveled platform 5 are dictated by the formula $A^2+B^2=C^2$, wherein A is the length of said beveled platform 5 from said insertion blade tip 6 to the back of the beveled platform 7, B is the height of the beveled platform 5 and C is the length of the ramp formed by the beveled platform insertion blade tip up to the height of said beveled platform. In some embodiments, the height of said beveled platform 5 is not to exceed 0.5 millimeters. In some embodiments, the length of said beveled platform 5 from said insertion blade tip 6 to the back of the beveled platform 7 is not to exceed 1.0 millimeters. In some embodiments, the width of said beveled platform 5 is not to exceed 0.35 millimeters. In some embodiments, said first end/beveled platform tip/insertion blade tip 6 comprises a fine surgical lancet. In some embodiments, said first end/beveled platform tip/insertion blade tip 6 comprises an angle of between 20 and 90 degrees. In some embodiments, said beveled platform 5 increases in thickness from a fine blade tip towards the second end/back of the beveled platform 7 in the direction of the Y-axis.

Figure 17:
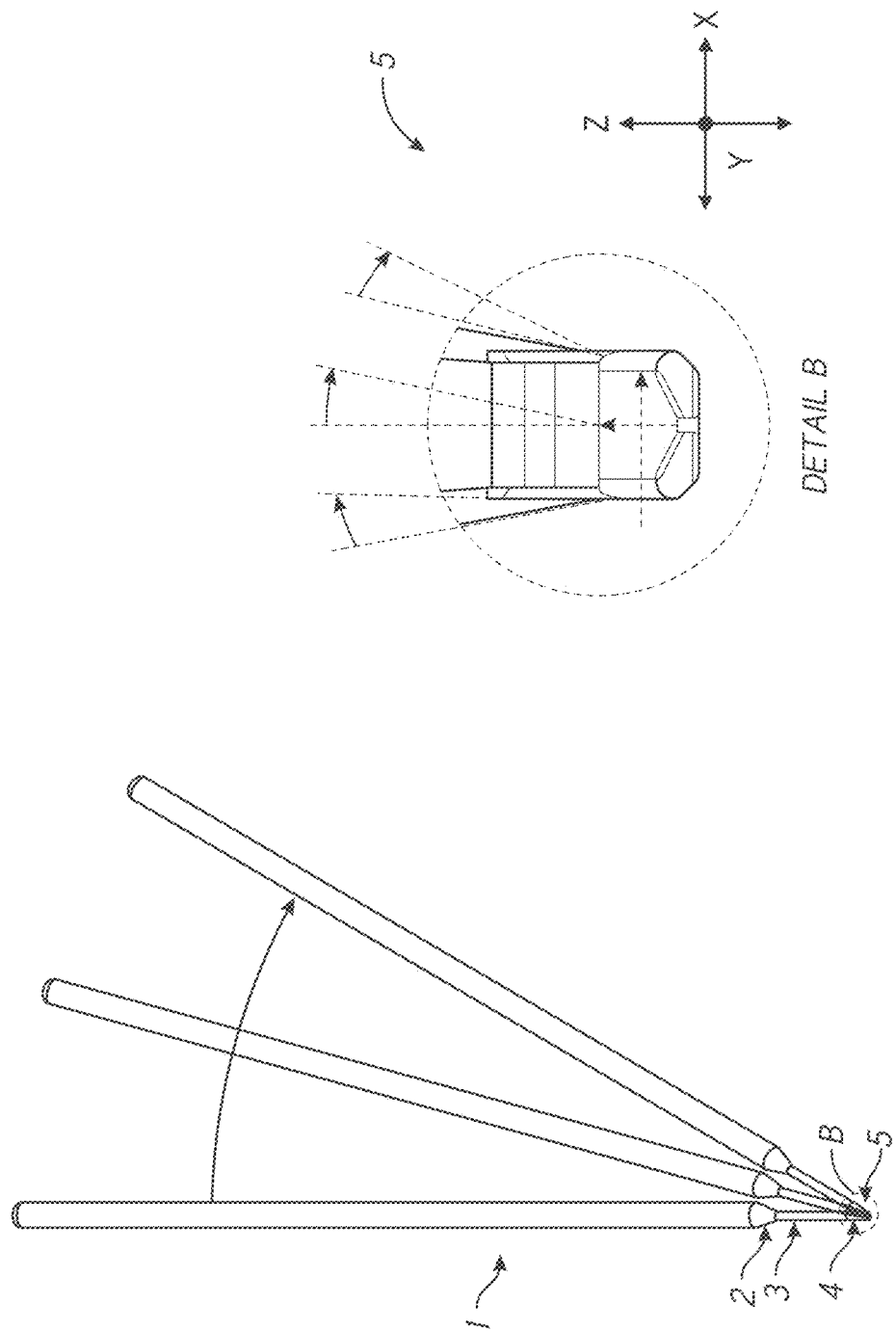
FIG. 17 shows a front face view of one embodiment of the device with an enlarged detailed view of the operative end of the device with the beveled platform 5. Shown are examples of the different angles of attachment of the handle 1 to the beveled platform 5 clockwise 0, 15, and 30 degrees relative to the Z-axis and X-axis. The increased platform thickness is also indicated as the platform extends from the insertion tip 6 towards the back of the platform 7 and from the first side (on the right) to the second side (on the left).
Figure 18A:
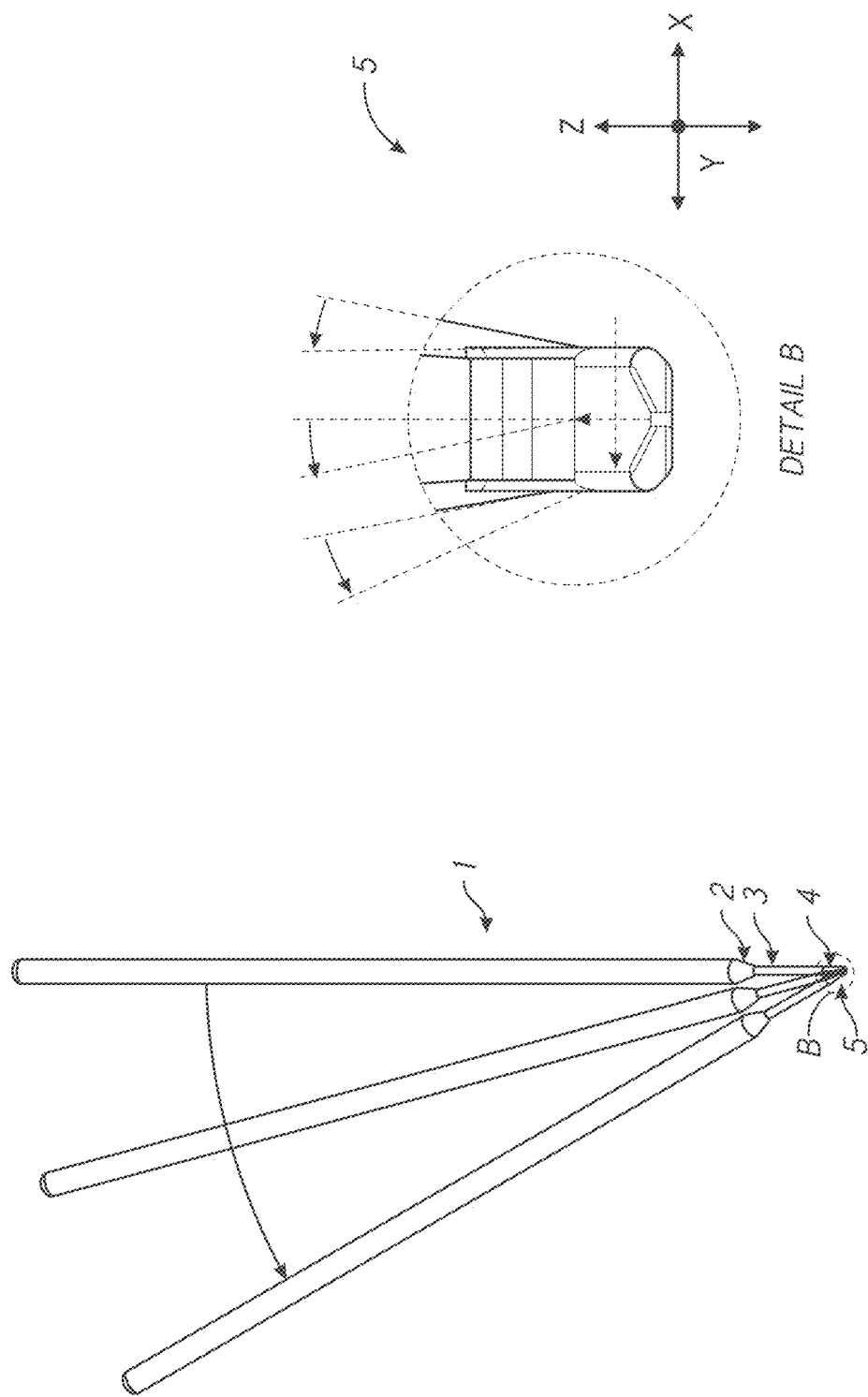
FIG. 18A shows a front face view of one embodiment of the device with an enlarged detailed view of the operative end of the device with the beveled platform 5. Shown are examples of the different angles of attachment of the handle 1 to the beveled platform 5 counterclockwise 0, 15, and 30 degrees relative to the Z-axis and X-axis. The increased platform thickness is also indicated as the platform extends from the insertion tip 6 towards the back of the platform 7 and from the second side (on the left) to the first side (on the right).
Figure 18B:
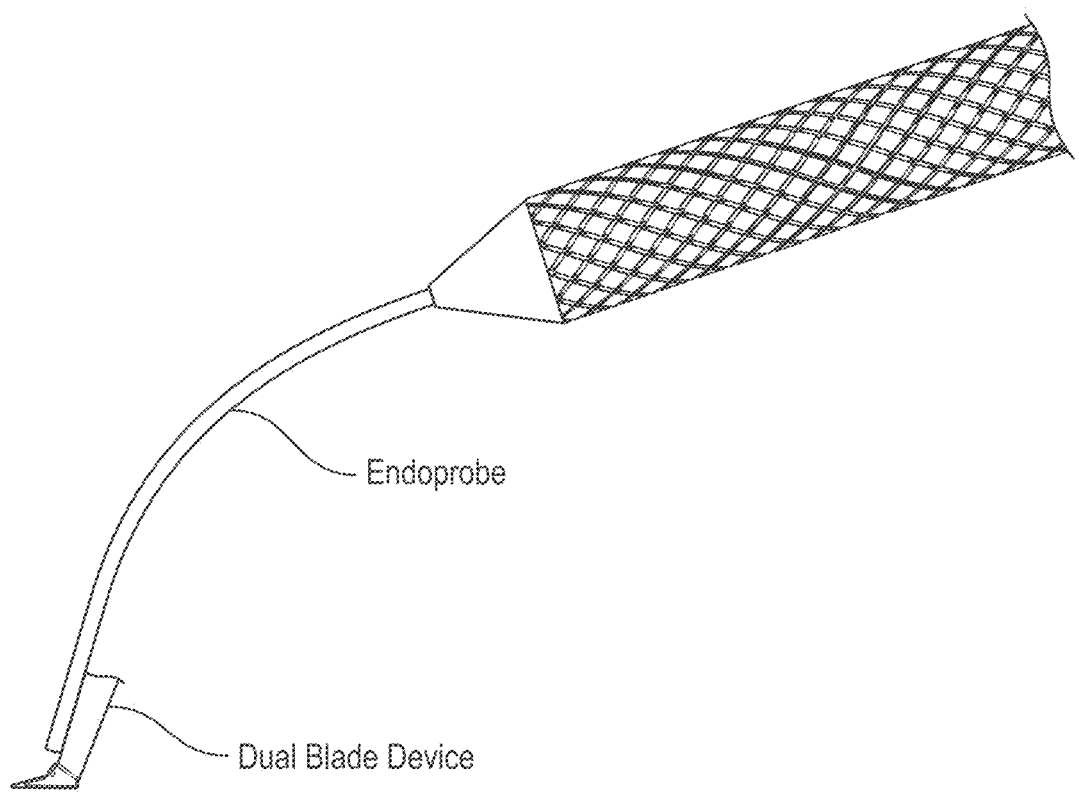
FIG. 18B shows one possible version of the device wherein it is integrated onto an endoscope.

In some embodiments, said first end/beveled platform tip/insertion blade tip 6 comprises a pointed tip with fine edges of surgical sharpness. In some embodiments, said first end/beveled platform tip/insertion blade tip 6 comprises a lancet. In some embodiments, said beveled platform 5 further comprises a first blade 10 and a second blade 11. In some embodiments, said first blade 10 is attached to a first side 8 of said second end/back of the beveled platform 7. In some embodiments, said first blade 10 and beveled platform 5 are operably attached at an angle ranging between 90 and 180 degrees in the Y-Z axis (shown in FIG. 15). In some embodiments, said angle is preferably between 90 and 120 degrees in the Y-Z axis (shown in FIG. 15). In some embodiments, said second blade 11 and beveled platform 5 are operably attached at an angle ranging between 90 and 120 degrees in the Y-Z axis (shown in FIG. 15). In some embodiments, said first blade 10 and handle 1 are operably positioned at an angle ranging between 90 and 120 degrees in the Y-Z axis (shown in FIG. 15). In some embodiments, said second blade 11 and handle 1 are operably positioned at an angle ranging between 90 and 120 degrees in the Y-Z axis (shown in FIG. 15). In some embodiments, said second blade 11 is attached to a second side 9 of said second end/back of the beveled platform 7. In some embodiments, said beveled platform 5 increases in thickness from said second side 9 towards the first side 8 in the direction of the X-axis (shown in FIG. 17). In some embodiments, said beveled platform 5 increases in thickness from said second side 9 towards the first side 8 in the direction of the X-axis and said beveled platform 5 increases in thickness from a fine blade tip of the first end 6 towards the second end/back of the beveled platform 7 in the direction of the Y-axis (shown in FIG. 17). In some embodiments, said beveled platform 5 increases in thickness from said first side 8 towards the second side 9 in the direction of the X-axis (shown in FIG. 18). In some embodiments, said beveled platform 5 increases in thickness from said first side 8 towards the second side 9 in the direction of the X-axis and said beveled platform 5 increases in thickness from a fine blade tip of the first end 6 towards the second end/back of the beveled platform 7 in the direction of the Y-axis (shown in FIG. 18). In some embodiments, said first blade 10 and said second blade 11 are parallel (shown in FIG. 15). In some embodiments, said first blade 10 and said second blade 11 extend above the top surface of said second end/back of the beveled platform 7. In some embodiments, said first blade 10 and said second blade 11 are positioned at an angle between approximately 100 to 140 degrees relative to the top surface of said second end/back of the beveled platform 7 (shown in FIG. 15). In some embodiments, said beveled platform 5 is approximately 0.3 millimeters wide. In some embodiments, said beveled platform 5 is approximately 0.2 millimeters wide. In a preferred embodiment, said beveled platform 5 is approximately 0.25 millimeters wide. In some embodiments, said beveled platform 5 is approximately 1.0 millimeters long. In some embodiments, said beveled platform 5 is approximately 0.4 millimeters high. In some embodiments, said highest point on the beveled platform 5 is the first and second blades. The device 12 (shown in FIG. 8, FIG. 10, FIG. 13, and FIG. 15) may be provided as a pre-sterilized, single-use disposable probe or tip that is attachable to a standard surgical handpiece.

It is not intended that embodiments of the present disclosure be limited to any particular construction material; however, it is believed that preferred materials include titanium, stainless steel, polyether ether ketone (PEEK), shape memory alloy, and shape memory polymers. In some embodiments, the present device is made from metal alloy materials. In some embodiments, the device of the present disclosure is rigid at room temperature, but is more flexible at body temperature. In some embodiments, the portions of the device of the present disclosure are rigid at room temperature, but are more flexible at body temperature. In some embodiments, portions of the device are made from different materials. In some embodiments, portions of the device are made from materials of various rigidity. In some embodiments, said tool shaft is flexible. In some embodiments, said tool shaft is made from a lower density material.

It is not intended that embodiments of the present disclosure be limited to any particular construction material; however, it is believed that preferred materials include titanium, stainless steel, polyether ether ketone (PEEK), shape memory alloy, and shape memory polymers. In some embodiments, the device of the present disclosure is rigid at room temperature, but is more flexible at body temperature. In some embodiments, the portions of the device of the present disclosure are rigid at room temperature, but are more flexible at body temperature. In some embodiments, portions of the device are made from different materials. In some embodiments, portions of the device are made from materials of various rigidity. In some embodiments, said tool shaft is flexible. In some embodiments, said tool shaft is made from a lower density material.

The tip may be formed of various metals or polymers that are rigid enough to support elevation of tissue such as TM. The blades may be made of the same materials as the distal tip and handle 1 or might be of a separate material that allows for greater tolerances for a razor edge (stainless steel or titanium). Shape memory polymers or alloys could be utilized to enhance functionality of the device by allowing for a change in confirmation after placing the device in the eye and exposing it to body heat. A movable sheath might be employed to cover the distal cutting tip during the insertion and removal steps from the eye so that the tip is not injured by movement across the clear corneal wound.

The device can be made of different colors such as blue or black so that it can be visualized through the semi translucent TM tissue for better guidance.

According to some embodiments, devices disclosed herein can be used for incising tissue, such as a trabecular meshwork. A device may be introduced through a clear corneal incision (incision size between 0.5 and 2.8 mm in width) and advanced through the anterior chamber either across the pupil or across the body of the iris to engage the trabecular meshwork (TM) on the opposite side of the anterior chamber. The anterior chamber may be filled with viscoelastic to stabilize the chamber during the procedure. As shown for example in FIG. 19A, once the target tissue 20 (e.g., TM) is reached, the tip 6 of the device may be then used to enter into Schlemm's canal ("SC") 22.

Figure 19A:
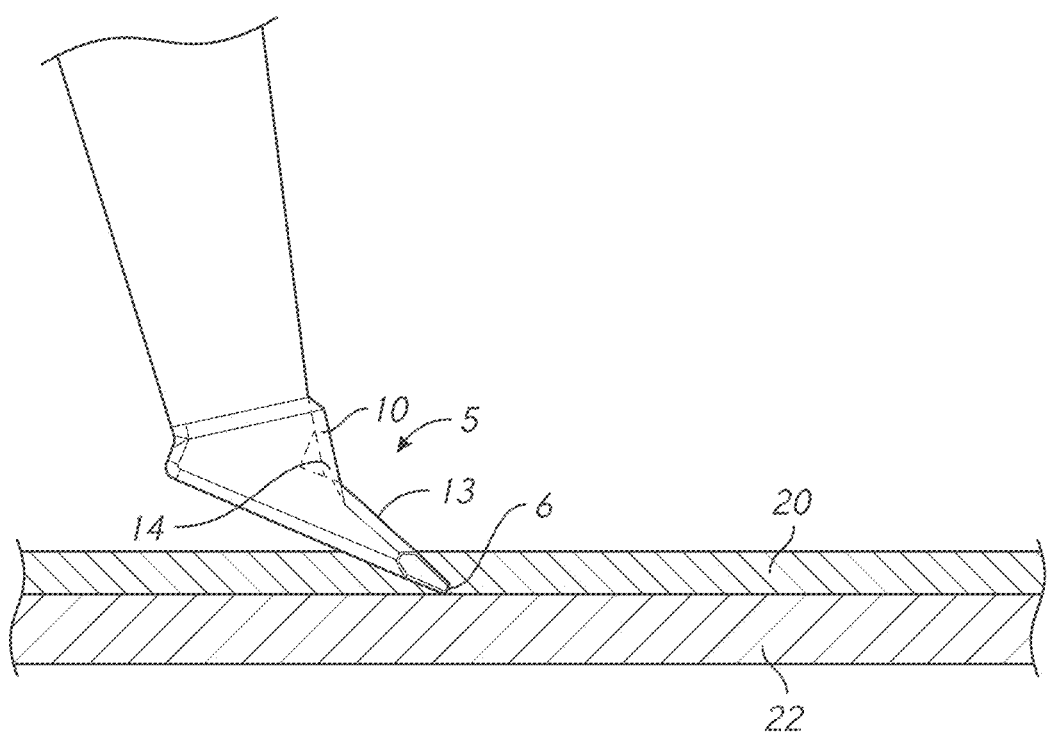
FIG. 19A shows a device applied to a trabecular meshwork and Schlemm's canal, according to some embodiments of the present disclosure.
Figure 19B:
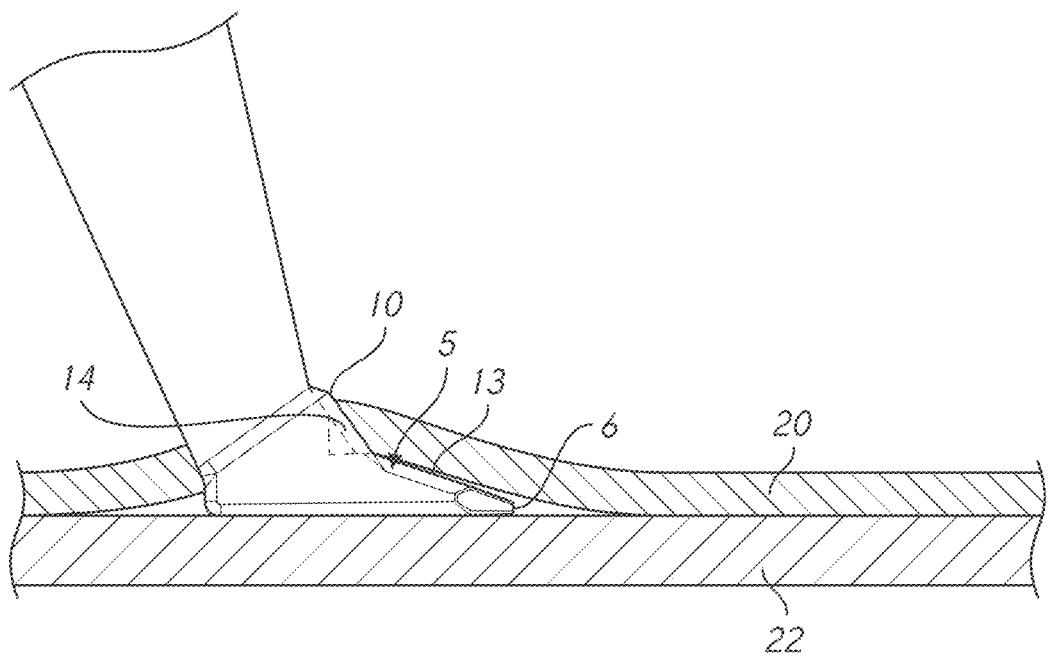
FIG. 19B shows a device elevating the trabecular meshwork away from the Schlemm's canal, according to some embodiments of the present disclosure.
Figure 19C:
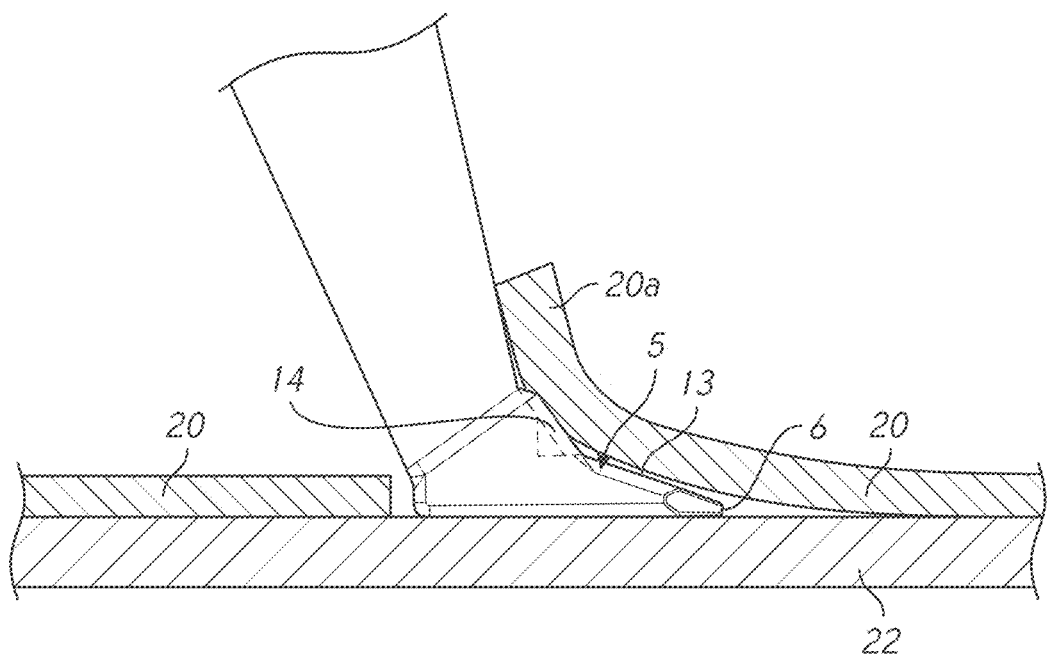
FIG. 19C shows a device incising the trabecular meshwork, according to some embodiments of the present disclosure.
Figure 19D:
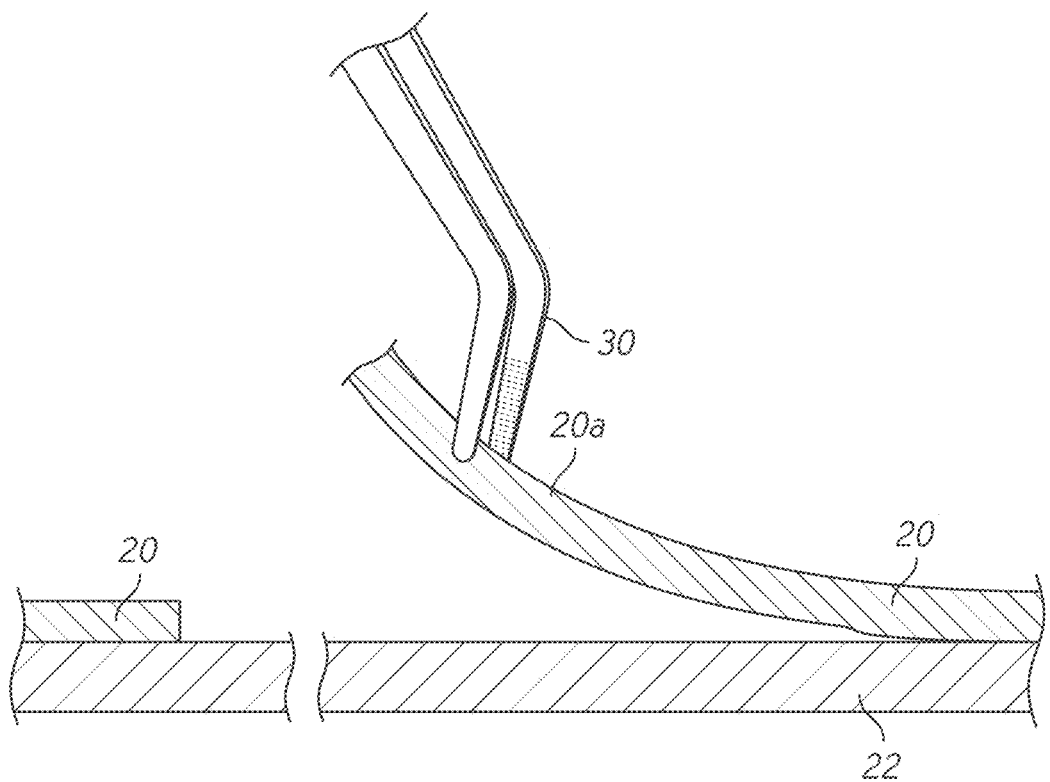
FIG. 19D shows a device engaging a strip of trabecular meshwork, according to some embodiments of the present disclosure.

According to some embodiments, for example as shown in FIG. 19A, the ramp 13 may be used to elevate the TM 20 away from the outer wall of the Schlemm's canal 22. According to some embodiments, for example as shown in FIG. 19B, the advancement of the platform 5 can stretch the TM 20 as it travels up the ramp 13 without tearing a strip 20a of the TM 20 that is on the ramp 13. For example, the first side 8 and the second side 9 can allow the TM 20 on the ramp 13 (e.g., distal to the first and second lateral blades 10, 11) to remain connected to the TM 20 that is not elevated by the ramp 13. As the TM 20 is elevated, it is under tension that is greater than the tension of the TM 20 when not elevated from the SC 22. Advancement of the ramp 13 facilitates presentation of the TM 20 to the first and second lateral blades 10, 11. According to some embodiments, for example as shown in FIG. 19C, the TM 20 contacts the first and second lateral blades 10, 11 while the TM 20 is elevated (e.g., stretched and/or under tension). In this configuration, the first and second lateral blades 10, 11 incise first and second incisions into the TM 20 to form the strip 20a of the TM 20. The incision is more easily and precisely made due to the elevation of the TM 20. During advancement of the platform 5, at least a portion of the strip 20a can be received within the gap 14 between the first and second lateral blades 10, 11. The strip 20a can have a width W that corresponds to the distance D across the gap 14. The width W can be measured along the X-axis, such as across the first and second incisions and transversely (e.g., orthogonally) to the direction of advancement of the device 12 to form the strip 20a. The distance D can be measured along the X-axis, such as across the first and second lateral blades 10, 11 and transversely (e.g., orthogonally) to the direction of advancement of the device 12 to form the strip 20a. According to some embodiments, for example as shown in FIG. 19D, the strip 20a that has been separated from a remainder of the TM 20 can be removed by a device 30 (e.g., forceps) or by aspiration.

The advancement of the platform 5 and the ramp 13 can proceed as the device advances clockwise or counterclockwise. The distal cutting portion is angled so that the dual blades are placed in optimum cutting position. This angle may be such that the cutting tip bends to conform to the area between Schwalbe's line and the scleral spur (SS), an area that encompasses SC. SC is narrow near the cornea and wider near the SS and thus an angled tip is best to present the tissue 20 to the two edges of the TM. The ramp 13 of the cutting tip may be angled so that the tissue 20 is constantly elevated towards the blade as the tip is advanced in circumferential pattern. Between the cutting tip and the first and second lateral blades 10, 11, the ramp 13 is shaped to avoid cutting tissue, such that the TM 20 that is elevated away from the outer wall of the Schlemm's canal 22 remains intact as it advances along the ramp 13. For example, the ramp 13 can include convex or beveled edges that are not sharp enough to cut the TM 20. Endoscopic visualization may also be used to guide the cutting. In some embodiments, the device of the present disclosure may be placed at the end of an endoscope, precluding the need for a gonio lens during treatment. In some embodiments, the device of the present disclosure may be place at the end of an endoscope and the TM may be engaged under direct visualization of the endoscope camera.

Figure 10:
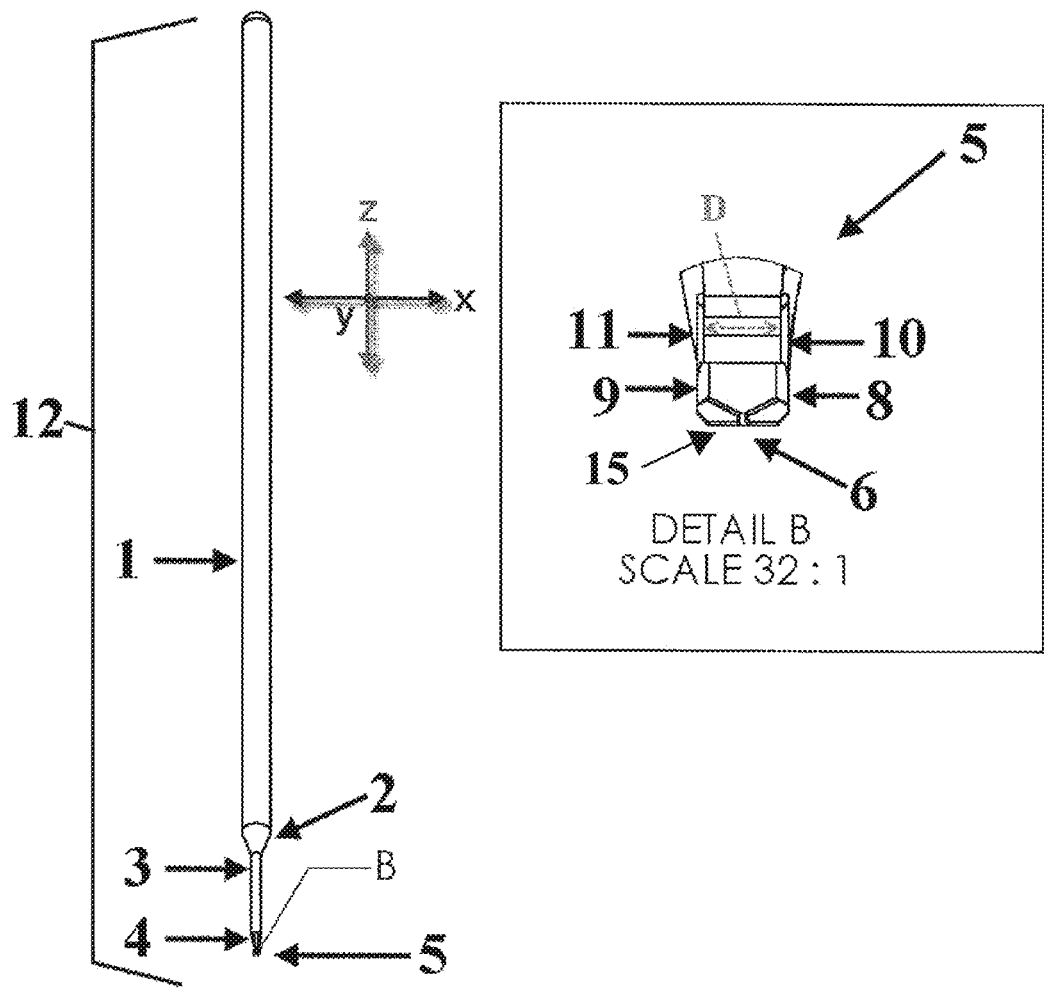
FIG. 10 shows a front face view of one embodiment of the device with an enlarged detailed view of the operative end of the device with the beveled platform.
Figure 11:
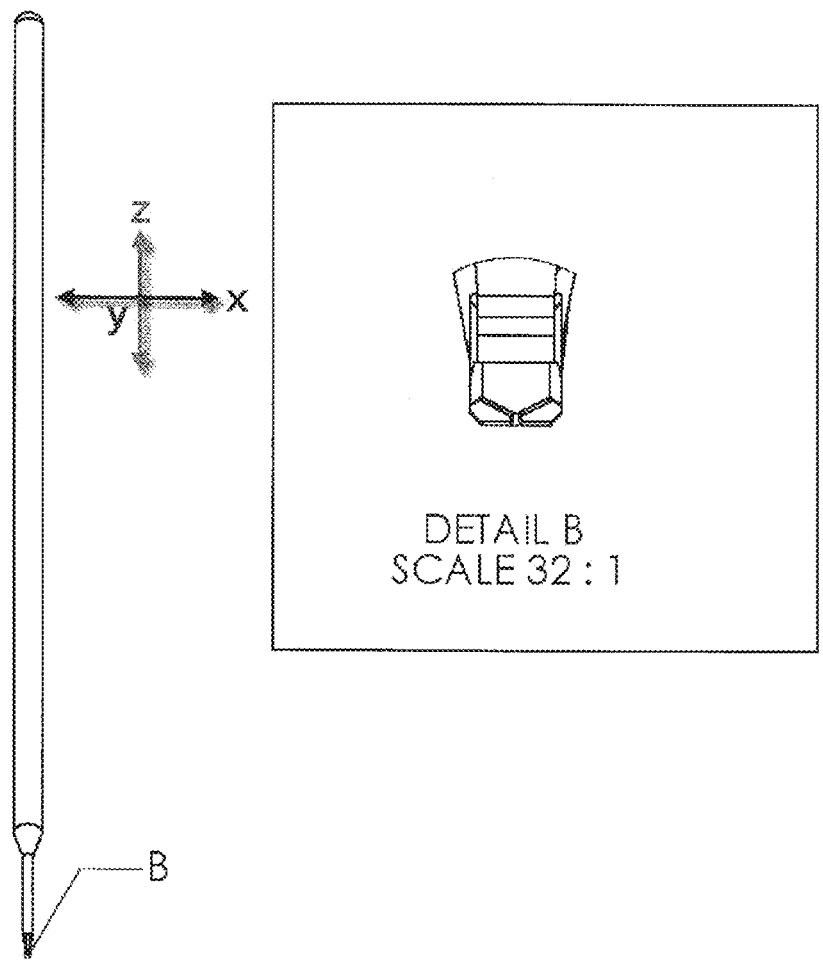
FIG. 11 shows a front face view of one embodiment of the device with an enlarged detailed view of the operative end of the device with the beveled platform 5. Measurements of specific parts are indicated.
Figure 12:
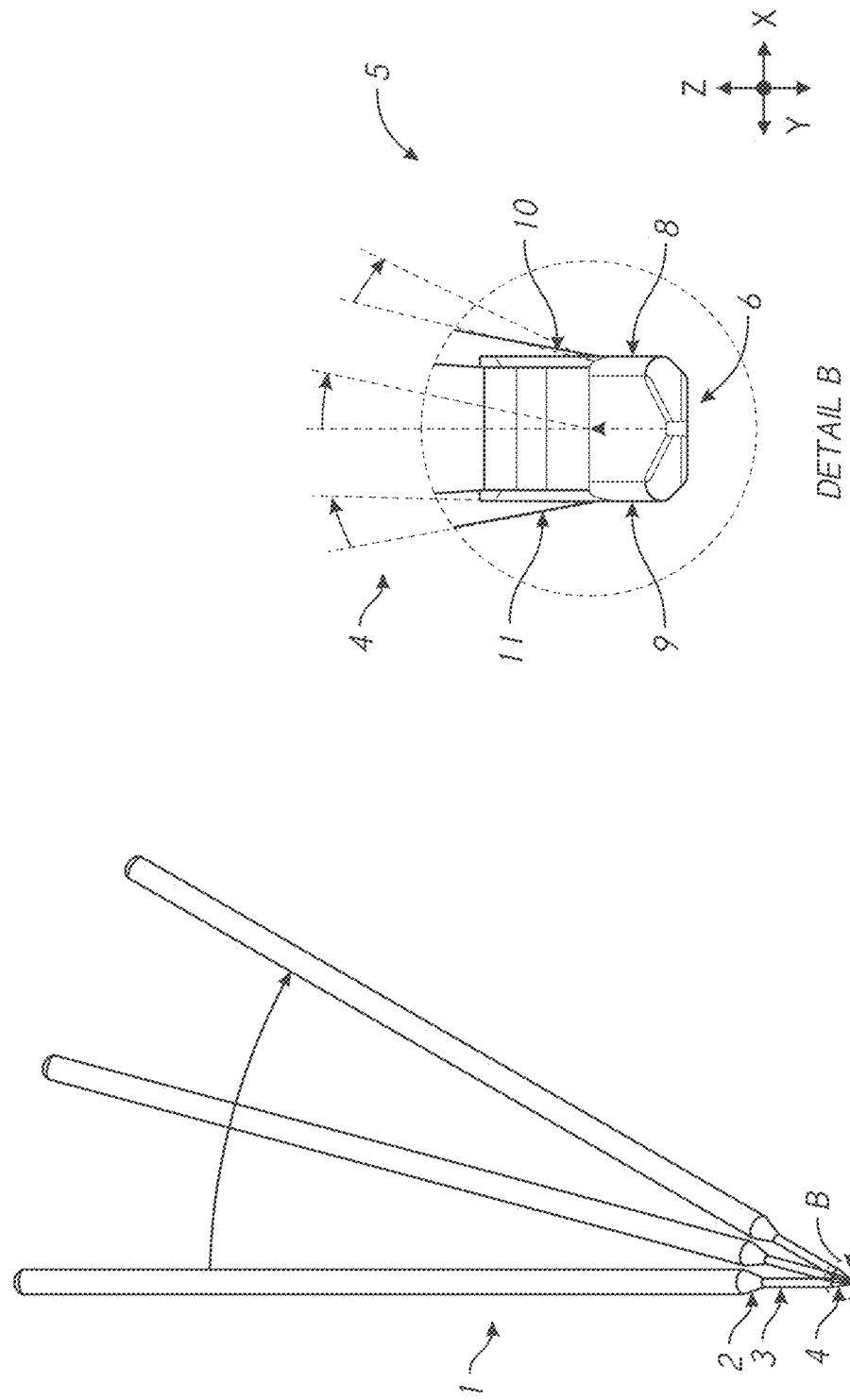
FIG. 12 shows a front face view of one embodiment of the device with an enlarged detailed view of the operative end of the device with the beveled platform 5. Shown are examples of the different angles of attachment of the handle 1 to the beveled platform 5 relative to the Z-axis. The increased platform thickness as the platform extends from the insertion tip 6 towards the back of the platform 7 is also indicated.
Figure 13:
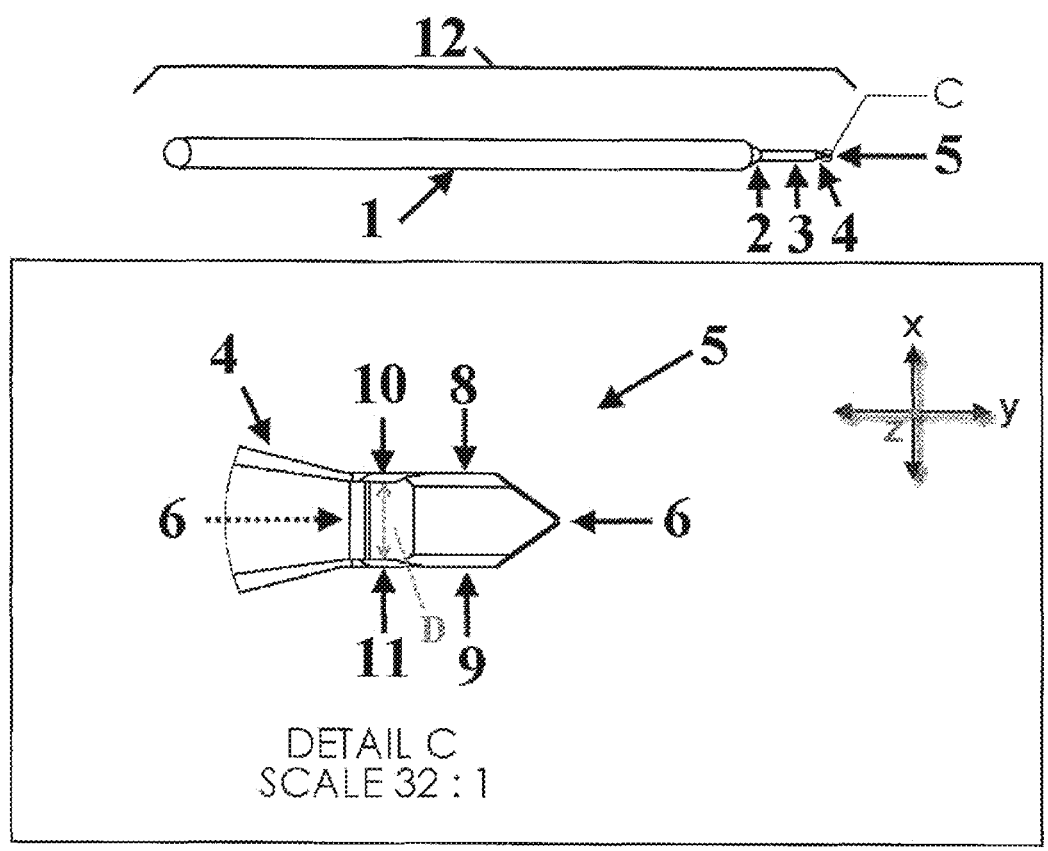
FIG. 13 shows a straight top view of one embodiment of the device with an enlarged detailed view of the operative end of the device with the beveled platform 5.
Figure 14:
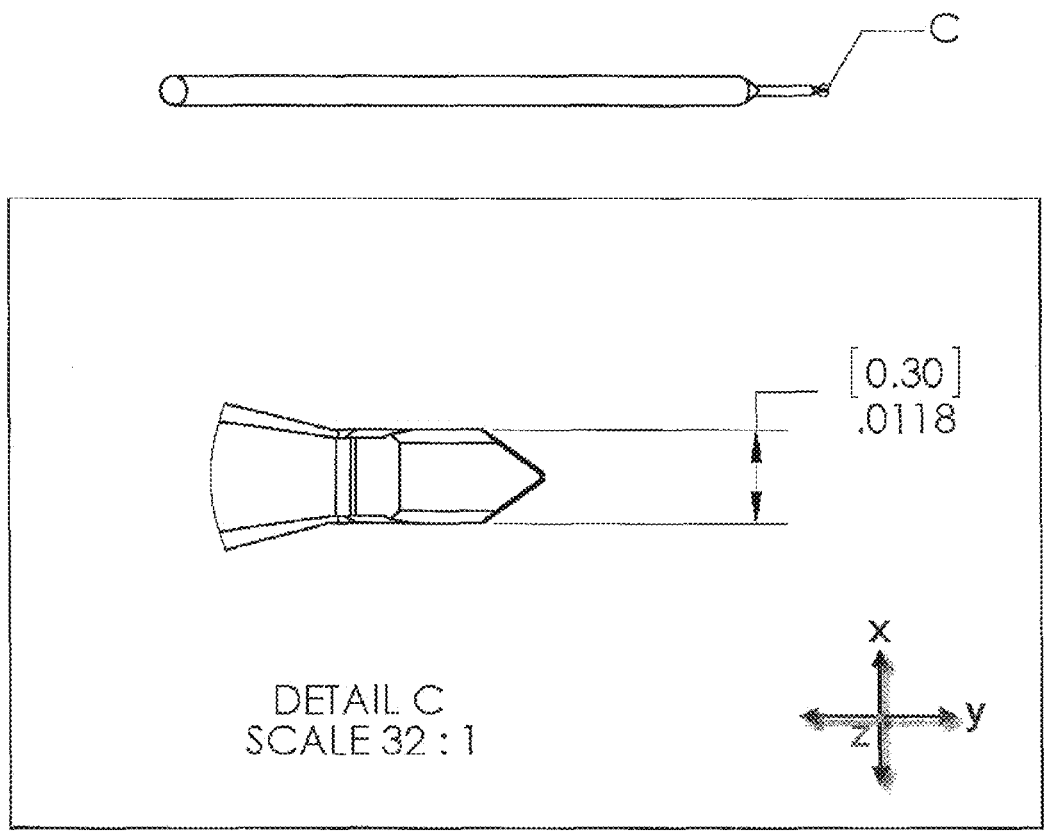
FIG. 14 shows a straight top view of one embodiment of the device with an enlarged detailed view of the operative end of the device with the beveled platform 5. Measurements of specific parts are indicated.
Figure 15:
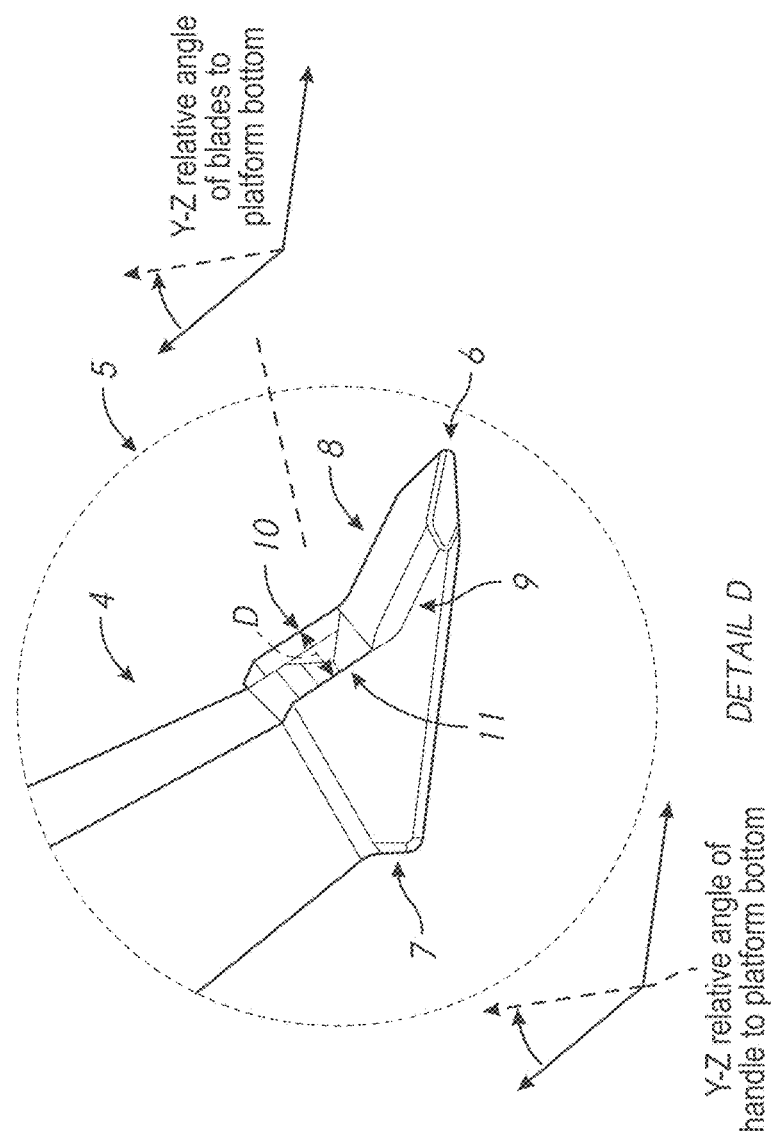
FIG. 15 shows an angled, side view of one embodiment of the device with an enlarged detailed view of the operative end of the device with the beveled platform 5. The shaded aspect provided a view of the dimensions of the beveled platform. The angle of tool shaft 4 attachment and of first and second blade attachment relative to the beveled platform 5 are indicated.
Figure 15:
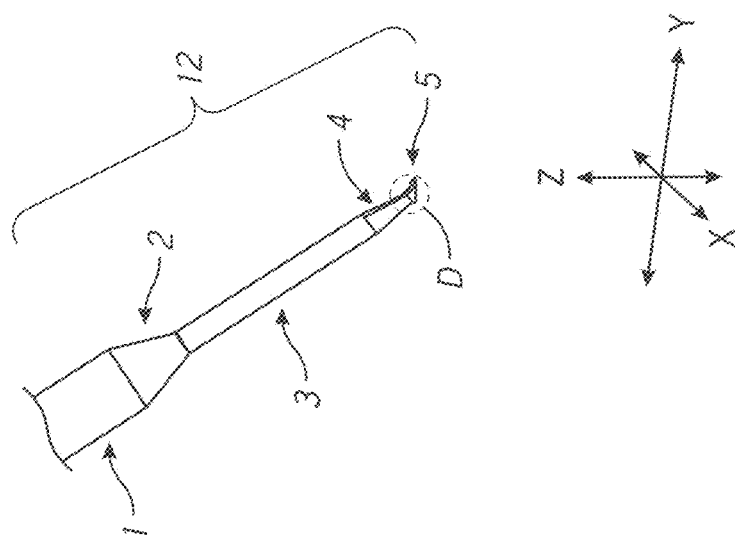
Figure 16:
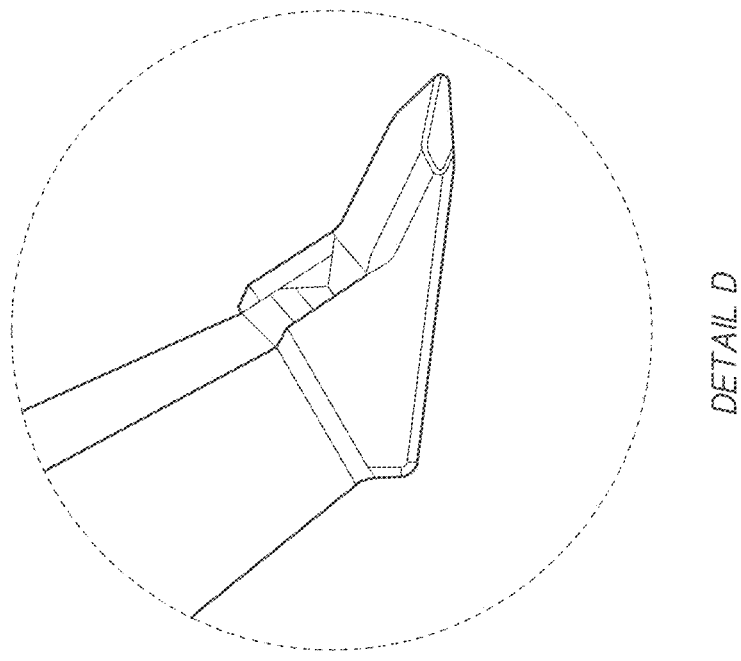
FIG. 16 shows an angled, side view of one embodiment of the device with an enlarged detailed view of the operative end of the device with the beveled platform 5. The shaded aspect provided a view of the dimensions of the beveled platform. Measurements of specific parts are indicated.
Figure 16:
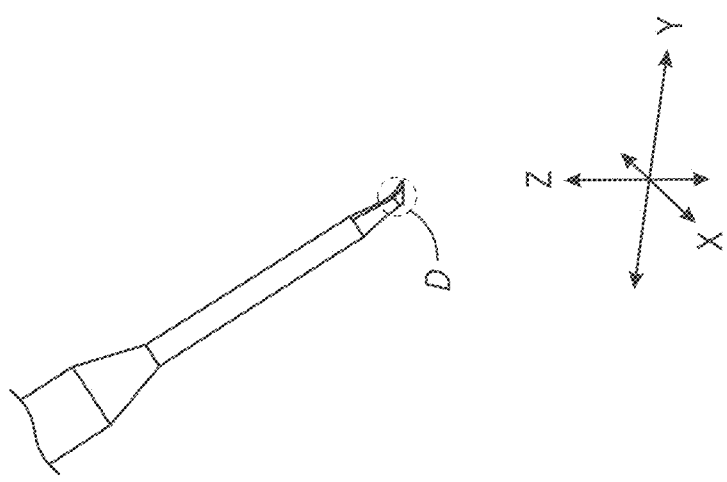

In some embodiments, a method for cutting a strip 20a of tissue 20 (e.g., TM) of width W from a tissue mass comprises the steps of: a) providing a device which comprises; i) a handle attached to a beveled platform, ii) an anterior insertion blade tip of the beveled platform expanding backwards to a posterior end of the beveled platform that is devoid of cutting features, iii) a first side of the beveled platform upon which is affixed a first lateral blade, iv) a second side of the beveled platform upon which is affixed a second lateral blade; v) at least first and second lateral cutting edges formed by blades in a generally perpendicular and posterior position to said opposite edges of said anterior insertion blade tip of the beveled platform, said first and second cutting edges being separated by a gap 14 of distance D that is approximately equal to the width W of the strip 20a of tissue 20 to be cut (this is shown in FIG. 10, FIG. 13, and FIG. 15); b) advancing the anterior insertion blade tip of the beveled platform through tissue 20 such that the first and second cutting edges are positioned adjacent to tissue 20 to be cut; c) advancing the distal end such that the cutting edges cut a strip 20a of tissue 20 of approximate width W and the cut strip 20a of tissue 20 remains substantially intact. In some embodiments, the mass of tissue 20 is in vivo. In some embodiments, the mass of tissue 20 is in vitro. In some embodiments, said device is integrated into an endoscope. In some embodiments, said cutting is under direct visualization. In some embodiments, the mass of tissue 20 is located within the body of a human or animal subject. In some embodiments, the strip 20a of tissue 20 is removed for a diagnostic or therapeutic purpose. In some embodiments, the subject suffers from glaucoma and wherein the method is carried out to remove a strip 20a of trabecular meshwork from an eye of the subject to facilitate drainage of aqueous humor from the eye thereby lowering intraocular pressure. In some embodiments, said eye has a dilated pupil. In some embodiments, step b comprises inserting the device into the anterior chamber of the eye; positioning the anterior insertion blade tip of the beveled platform adjacent to or within the trabecular meshwork of the eye; and advancing the cutting tube such that the cutting edges cut a strip 20a of approximate width W from the trabecular meshwork. In some embodiments, the device provided in step a of the method further comprises an anterior insertion blade tip of the beveled platform and wherein the anterior insertion blade tip of the beveled platform is advanced through the trabecular meshwork and into Schlemm's canal and, thereafter, the anterior insertion blade tip of the beveled platform is advanced through Schlemm's canal as the cutting tube is advanced to cut the strip 20a of tissue 20. In some embodiments, the device provided in step a further comprises apparatus for severing the strip 20a of tissue 20 after the strip 20a of tissue 20 has reached a desired length and wherein the method further comprises the step of severing the strip 20a of tissue after the strip 20a of tissue 20 has reached a desired length. In some embodiments, the method is carried out to form an incision in skin, mucous membrane, an organ, a tumor or other anatomical structure. In some embodiments, the method is carried out to remove tissue 20 from the vascular system. In some embodiments, the method is carried out to remove tissue 20 from the lymphatic system. In some embodiments, the method further comprises the step of: c) removing the strip 20a of tissue 20.

It is not intended that embodiments of the present disclosure be limited to any particular endoscope; it is believed that the device may be optimally designed for an ophthalmic endoscopy system endoscope. One such system is commercially called "Endo Optiks."

The device could have a distal port that allows for injection of fluid to deliver local balanced salt solution, medication, viscoelastics or therapeutic agents or to wash away reflux of blood that occurs during this type of procedure. The ultimate goal of this procedure may be to remove entire segments of TM without leaving significant leaflets of tissue behind (something that occurs with other devices that cut TM without conforming to the space of interest). The procedure might be combined with cataract extraction and can be performed before or after the cataract extraction and while the pupil is dilated. The procedure might be coupled with other intraocular surgery such as iris or vitreous/retina based procedures.

Conditions that might benefit from use of this device include:

1. Primary open angle glaucoma
2. Normal or Low tension glaucoma
3. Pseudoexfoliation glaucoma
4. Pigment dispersion glaucoma
5. Angle closure glaucoma (acute, subacute, chronic)
6. Neo vascular or inflammatory glaucoma
7. Ocular hypertension
8. Other types of glaucoma that are related to high intraocular pressure The device could be used for research purposes to harvest TM or other small sheath of tissue for lab based studies or to harvest cells for in vitro culture needs. The device can be used to cut Anterior Synechiae or other cellular or fibrovascular membranes over the drainage angle such as those seen with ICE syndrome or neovascular glaucoma.

It is not intended that embodiments of the present disclosure be limited to any particular method, medical target, or device confirmation; however, it is believed that the device may be optimally designed to remove trabecular meshwork of the eye, unroofing small vessels (such as veins, arteries, lymphatic vessels, or other vessel with a lumen), and for creating a hole or opening in the tympanic membrane of the ear. It is not intended that embodiments of the present disclosure be limited to any particular mechanism; however, it is believed that creating an opening in the tympanic membrane of the ear may help aid in treating ear disease.

EXAMPLES

Figure 20:
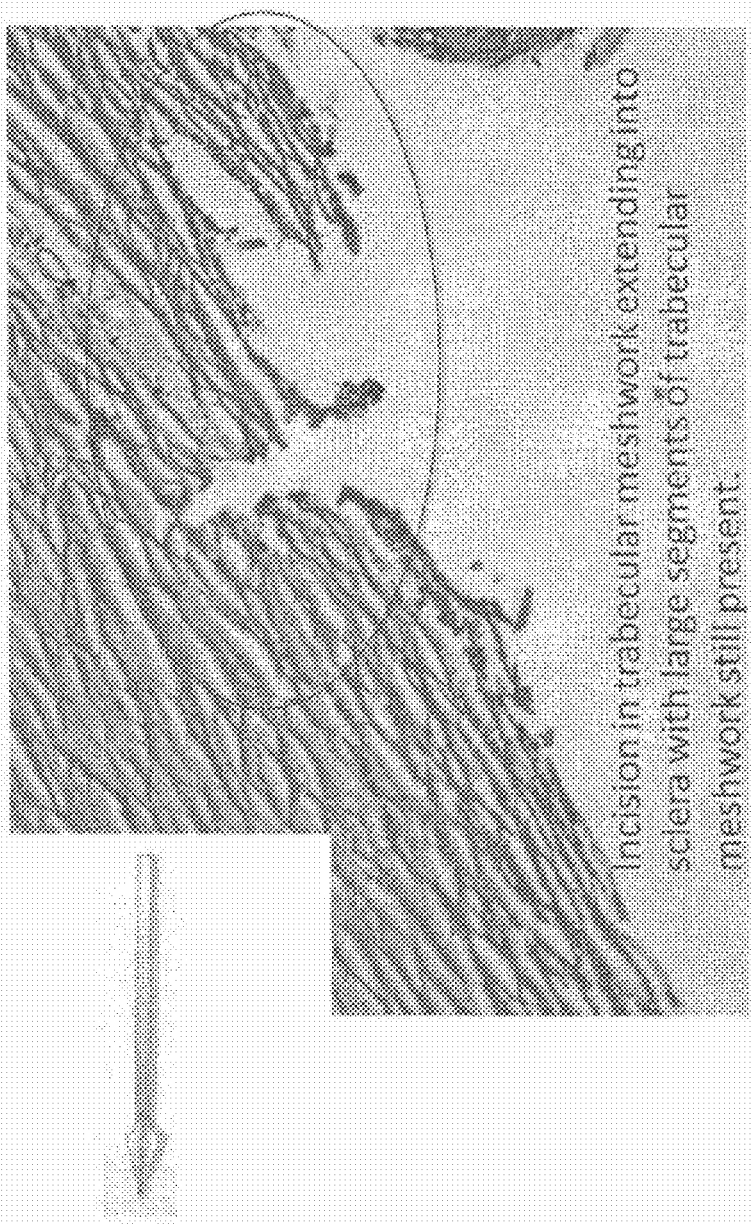
FIG. 20 shows an incision in trabecular meshwork extending into sclera with large segments of trabecular meshwork still present.

Procedures using traditional incisional goniotomy have certain disadvantages. FIG. 20 shows an incision in trabecular meshwork extending into sclera with large segments of trabecular meshwork still present. For this procedure (considered the gold standard surgery for "cutting" through the trabecular meshwork and traditionally called "goniotomy") an MVR blade was used to create a single incision in the trabecular meshwork to create an opening into Schlemm's canal. In this photo, there is a histological sample from a procedure in which an incision exists through Trabecular meshwork and extends into sclera. There are large leaflets of trabecular meshwork remaining on either side of the incision. These leaflets scar down and close the opening that was created into Schlemm's canal. This precludes any long-term benefit in intraocular pressure lowering which is the goal of the surgery.

Figure 21:
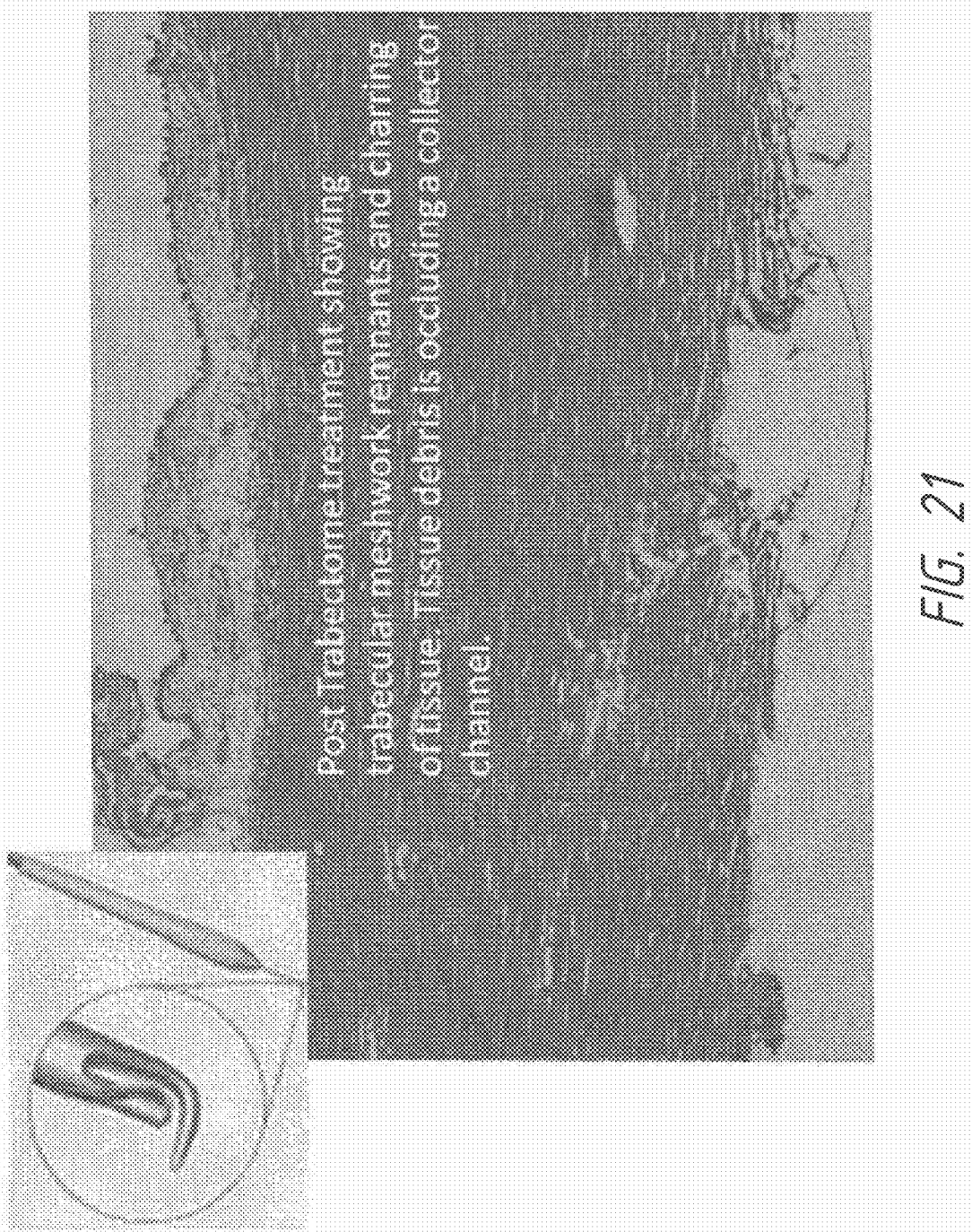
FIG. 21 shows post-Trabectome® treatment showing trabecular meshwork remnants and charring of tissue. Tissue debris is occluding a collector channel.

Procedures using a Trabectome® device also have certain disadvantages. For such a procedure (designed to replace goniotomy and to improve upon that procedure by removing sections of trabecular meshwork) a Trabectome® device was used to engage the trabecular meshwork and cautery was applied to the trabecular meshwork, as shown in FIG. 21. The circle shows an area where a small segment of trabecular meshwork was removed; however, there are large leaflets of trabecular meshwork remaining and charred tissue on either side of the treatment area. FIG. 21 shows post Trabectome® treatment showing trabecular meshwork remnants and charring of tissue. Tissue debris is occluding a collector channel this device "burns" tissue and the burning of tissue creates inflammation that leads to more scar formation that leads to failure of the surgically induced opening into Schlemm's canal. In addition, due to cautery, many bubbles are formed during the procedure that makes visualization difficult during the actual procedure. These issues do not occur with embodiments of the present disclosure, which is a major advantage.

Figure 22:
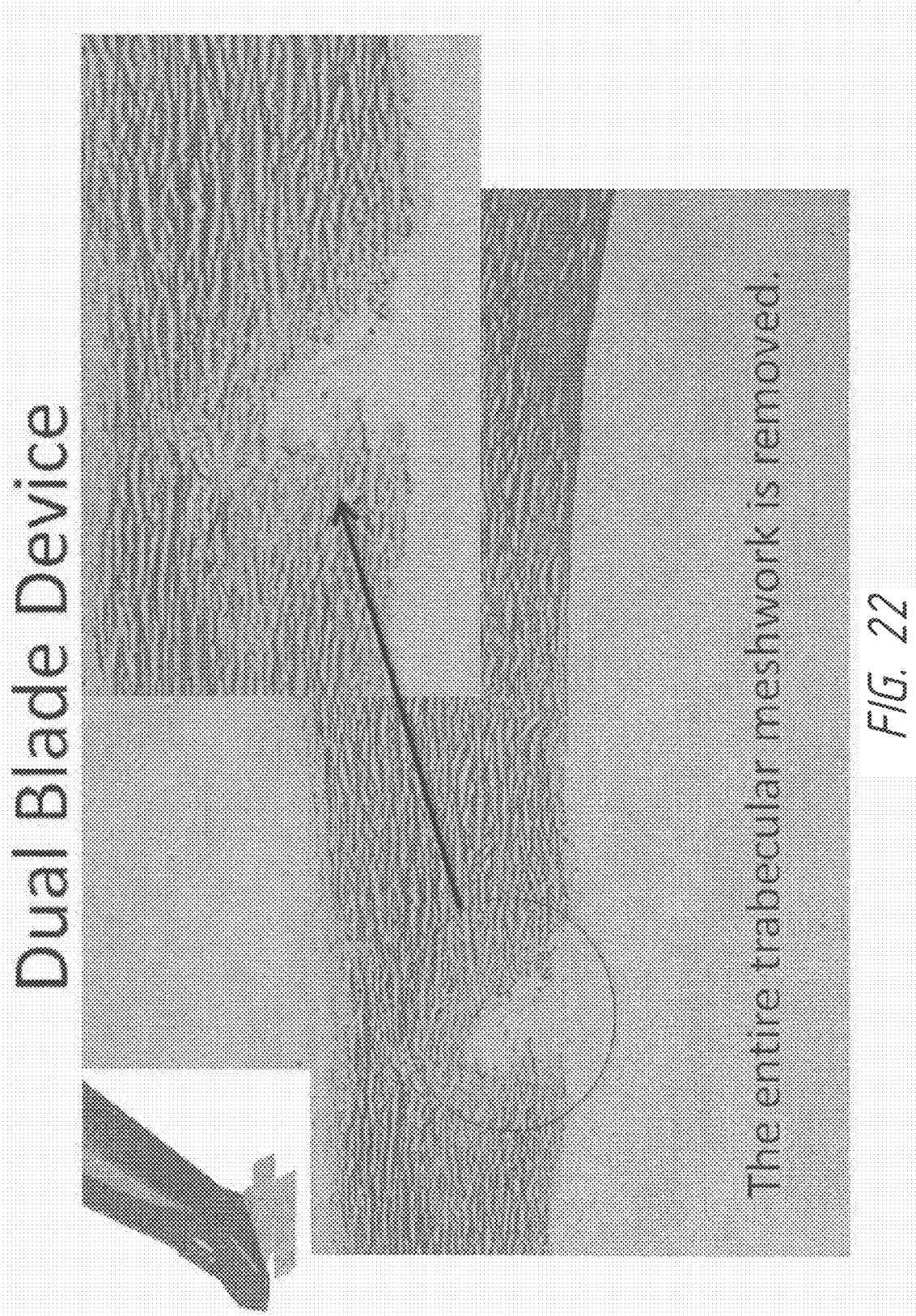
FIG. 22 shows tissue after treatment with a device according to embodiments of the present disclosure.

FIG. 22 shows tissue after treatment with a device according to embodiments of the present disclosure. The data shows complete removal of trabecular meshwork with no remaining leaflets without any evidence of tissue burning. The inset photo in FIG. 22 shows a close up of the circled area. A representative photo of a device is in the inset on the left of FIG. 22.

Figure 23:
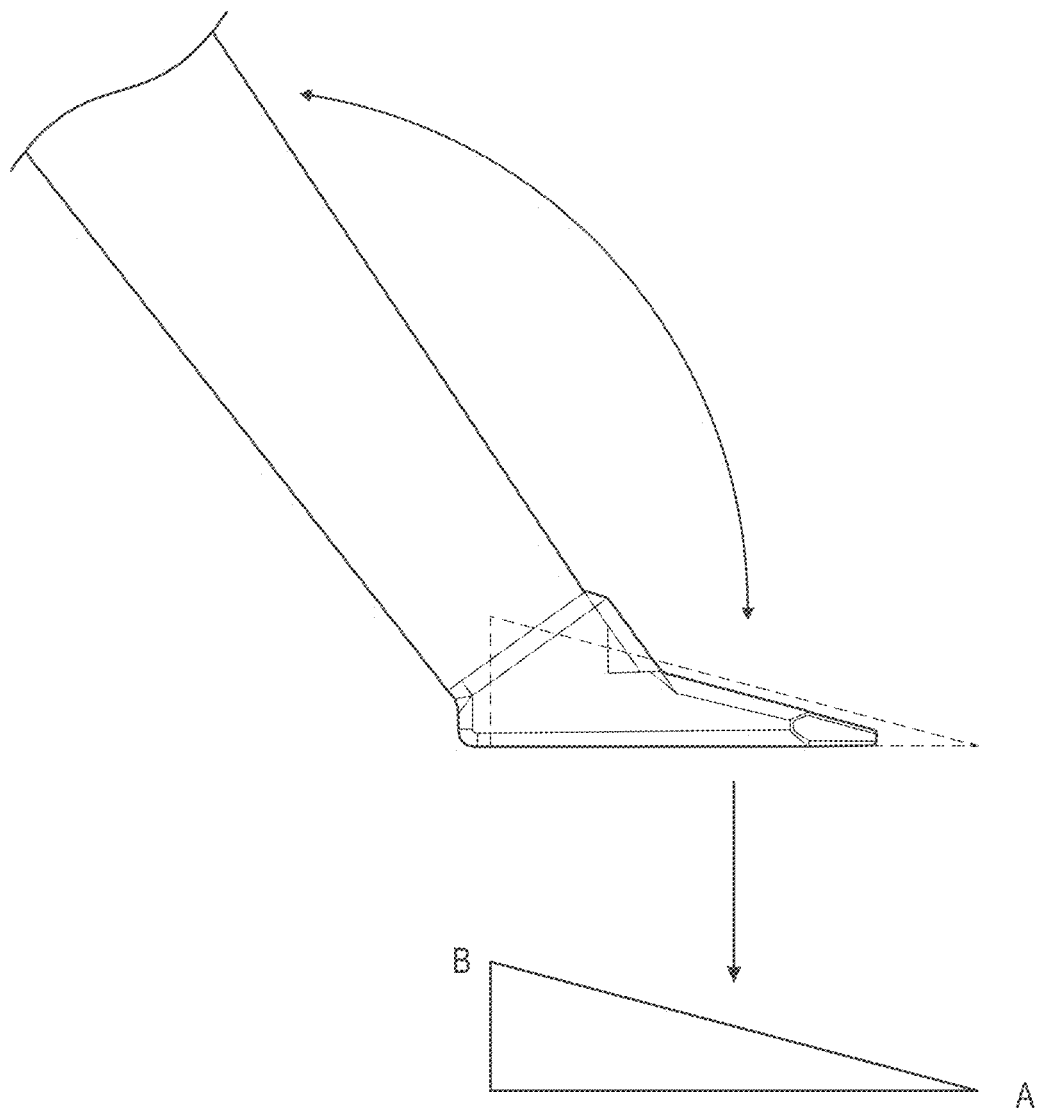
FIG. 23 shows another description of the configuration of the dual blade device according to embodiments of the present disclosure.

There is a second angle between the handle 1 and the ramp 13 that is not illustrated in FIG. 23. The ramp 13 does not only form an angle with the handle 1 as shown in the picture to the right in FIG. 23. It also forms an angle in the z axis. (The pivot is at the "#") away from the page as viewed. In some embodiments, the angle between the handle 1 and the ramp 13 ranges between approximately 90 and 120 degrees. It is believed that the ramp 13 pierces the tissue wherein the tissue then slides up the ramp 13 from A to B. The blades (*) then cut the tissue as the device is advanced.

There exists a disadvantage of a conventional blade where the foot plate is sitting in Schlemm's canal. Because there is no ramp 13 and no second angle between the tip and the handle, a second angle would have a pivot at the "*" which would create a pivot of the device inferiorly at the ramp 13.

Figure 24:
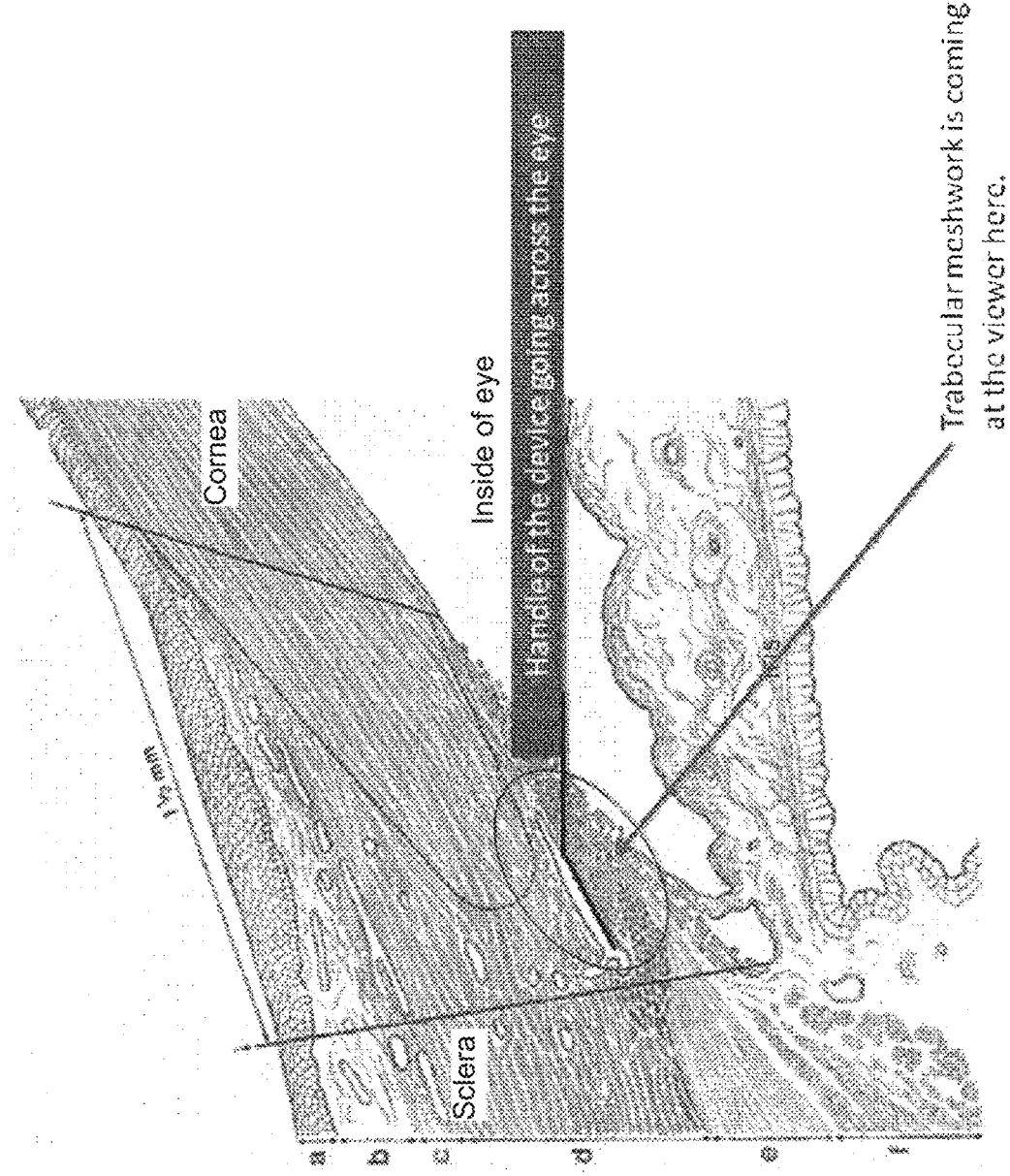
FIG. 24 shows the anatomy of interest at a cross section of the eye. The handle 1 is in the eye and going across to the opposite side Schlemm's canal outlined by a circle. The angle between the handle 1 and the ramp will allow the blade to enter Schlemm's canal and cut tissue. That first angle would make the ramp come out towards the viewer. However, a second angle would also need to exist that follows the black lines to allow the device to also fit in the angles space of Schlemm's canal.

FIG. 24 shows a cross section of the eye where one embodiment of handle 1 is in the eye and going across to the opposite side Schlemm's canal outlined by a circle. The angle between the handle 1 and the ramp 13 will allow the blade to enter Schlemm's canal and cut tissue. In this figure, that first angle would make the ramp 13 come out towards the viewer. However, a second angle would also need to exist that follows the black lines to allow the device to also fit in the angles space of Schlemm's canal.

Approval for a preclinical study was obtained from the Colorado Multiple Institutional Review Board for the use of human material prior to initiation of the study and the tenets of the Declaration of Helsinki were followed. Informed consent was obtained from donors or relatives for use in research by the eye bank from which human globes were obtained.

For histologic analyses, 6 corneal rim specimens were obtained from the Rocky Mountain Lions Eye Bank (Aurora, Colorado, USA) and the San Diego Eye Bank (San Diego, California, USA). Tissue samples were removed from the storage medium and mounted on a platform with the TM side facing up and secured in place using tissue pins. A total of 2 samples were used for each of the 3 treatment methods studied. An MVR blade was used to create a single incision in the central TM under microscopic visualization along the length of 2 corneal rims. For the Trabectome® device, the foot plate of the device tip was inserted into the Schlemm's canal under microscopic visualization. Once in place, the foot pedal was used to apply continuous ablation while advancing the tip slowly across the extent of the TM sample. A standard power setting of 0.8 W was used during treatment. The dual-blade device was used to incise the TM of 2 samples. The blade tip was used to incise TM in a manner similar to that used for goniotomy and the blade was then advanced in a clockwise fashion along the extent of the TM. At the distal end, the blade tip was tilted upwards to incise a complete ribbon of TM and the process was repeated in a counterclockwise fashion to incise the remaining TM tissue.

All tissue samples were then immediately preserved in 4% paraformaldehyde/phosphate-buffered saline overnight at 4° C. and then radially cut into quadrants. Rim sections were processed for histology and embedded into paraffin so that the cut edge of the tissue was facing the front of the block. Tissue sections (6 mm thick) were cut and stained with Mayer's hematoxylin-eosin Y (Richard-Allan Scientific, Kalamazoo, Michigan, USA). Bright-field imaging was performed using a Nikon Eclipse 80i microscope (Nikon, Melville, New York, USA) equipped with a Nikon D5-Fil color camera and a Nikon CFI 103/Plan Fluor objective lens.

Human eye perfusion Studies: A total of 12 human globes from pseudophakic donors with no history of glaucoma were obtained from various eye banks around the country for perfusion studies on each device. The perfusion system used a standard programmable syringe pump (Pump 11 Plus; Harvard Apparatus, Holliston, Massachusetts, USA). Pressure was monitored via an in-line real-time pressure transducer (Research Grade Pressure Transducer; Harvard Apparatus) connected to a single-channel chart recorder (Pharmacia REC-481; Pharmacia/Pfizer New York, New York, USA). Polyethylene tubing with a 1.14 mm inner diameter (PE-160; Warner Instruments, Hamden, Connecticut, USA) was used for all connections.

In each case, the human globe was first prepared by injecting Dulbecco's modified Eagle medium (DMEM;

Invitrogen/Life Technologies, Carlsbad, California, USA) through the optic nerve with a 26-gauge needle until the globe had returned to a spherical shape. The perfusion line (terminating in another 26-gauge needle) was inserted diagonally through the anterior chamber of the eye, passing through the cornea and pupil and ending with the tip beneath the iris. The globe was surrounded by damp gauze and the perfusion pump (filled with DMEM) was set to an initial inflow rate of 7 mL/min. IOP was allowed to increase until it reached 30 mm Hg. The infusion rate was then reduced to 2-5 mL/min to maintain a steady-state IOP for at least 60 minutes prior to TM incision. A preoperative IOP was measured immediately prior to incision in each case. A 1.7 mm stainless steel keratome blade (BD) was used create a tri-beveled clear corneal incision near the limbus, and the anterior chamber was filled with enough viscoelastic (HealonGV; Abbott Medical Optics, Abbott Park, Illinois, USA) to maintain the anterior chamber and provide adequate visualization during the procedure in each case. Each technique was performed under gonioscopic view using a standard direct gonioscope with microscope assistance. The surgical procedure used for each device is described above. In each case, approximately 100-180 degrees of TM was treated. For each device, treatment was started 180 degrees away from the corneal wound and extended along the angle in a clockwise direction. The device was then extended in a counterclockwise direction from the same starting point. Every effort was made to treat the maximum amount of degrees possible with each device. In the case of the dual-blade device and Trabectome®, the instrument was rotated 180 degrees after the initial pass to direct the device tip in the direction of treatment. IOP was allowed to reach a steady state before measuring the postprocedure IOP. Each of the 3 studied surgical techniques was performed on a total of 4 eyes.

The mean and standard deviation of preprocedure and postprocedure IOP was calculated for each device as well as percent change in IOP. Student paired t tests were used to compare preprocedure and postprocedure IOP for each device. A calculated P value <0.05 was considered to be statistically significant.

Two corneal rim sections were analyzed for each device. Six-micron-thick histologic sections were taken from various clock hours treated with each device and stained with Mayer's hematoxylin-eosin Y (Richard-Allan Scientific).

Figure 2:
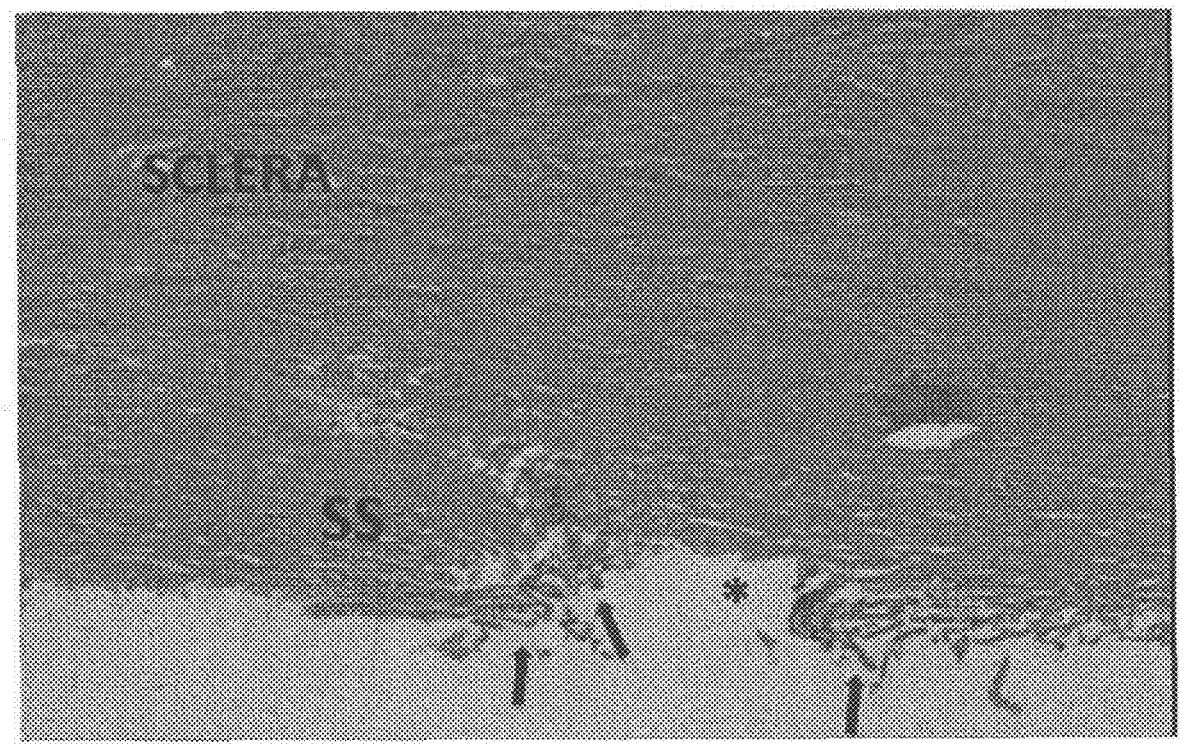
FIG. 2 shows a representative histologic specimen of human anterior chamber angle structures following incision with a Trabectome®. The incision extends through the full-thickness of a trabecular meshwork without damage to adjacent sclera. A portion of trabecular meshwork has been removed centrally with a moderate amount of residual tissue on either side of the incision (black arrows). Charring of the incision edges is noted. An asterisk labels the Schlemm's canal. SS=scleral spur. Light micrograph, hematoxylin eosin, magnification ×100.
Figure 3:
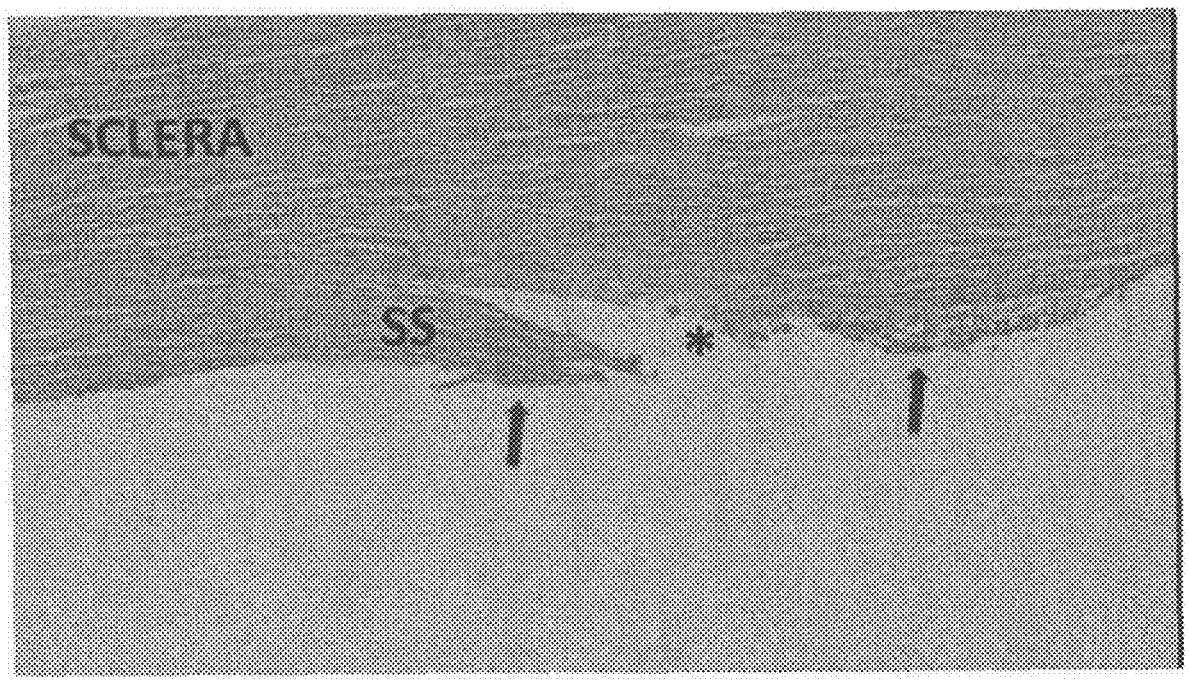
FIG. 3 shows a representative histologic specimen of human anterior chamber angle structures following an incision with a dual blade device. The incision extends through the full-thickness of a trabecular meshwork without injury to adjacent sclera. A near-complete removal of trabecular meshwork tissue has been accomplished (black arrows). An asterisk labels the Schlemm's canal. SS=scleral spur. Light micrograph, hematoxylin-eosin, magnification ×100.

Findings were consistent across all sections from each device tested. Cuts with the MVR blade exhibited complete incision through the entire thickness of TM tissue. However, there was minimal removal of TM with large leaflets of tissue remaining over the Schlemm's canal. The incision extended deeply through the Schlemm's canal with obvious injury to the adjacent deep sclera in the majority of sections (FIG. 1). The Trabectome® also achieved an opening through the entirety of TM tissue into the Schlemm's canal. Although the device also removed a large portion of the central TM, significant leaflets of residual tissue still remained. The residual TM demonstrated extensive charring from thermal injury. Tissue debris was also noted to be occluding distal collector channels (FIG. 2). Tissue incised with the dual-blade device demonstrated a more complete removal of TM without collateral damage (FIG. 3).

Data from human eye perfusion studies are included in Table 1. The extent of TM treatment varied between devices and between eyes from 100 to 180 degrees. All 3 treatment modalities achieved a significant reduction in measured IOP 30 minutes after treatment. Treatment with the dual-blade device and Trabectome® resulted in a mean IOP reduction of 40% each, whereas the MVR blade achieved a 31% reduction. Although the percentage of IOP decrease was greater for Trabectome® and the dual-blade device, there was no statistically significant difference in the IOP lowering between devices (dual-blade/MVR P=0.13; dual-blade/Trabectome® P=0.96; Trabectome®/MVR P=0.12). There was no correlation between the number of degrees of TM treated and the percentage IOP change for any device (r2=0.077-0.271).

TABLE 1

Human Eye Perfusion Studies After Treatment of Trabecular Meshwork by Various Devices

|  | Eye | Degrees of Angle Treated | Preprocedure IOP | Postprocedure IOP | Absolute IOP Change | Percent IOP Change | P Value |
|---|---|---|---|---|---|---|---|
| Dual-blade device | 1 | 140 | 17 | 10 | −7 | −41 |  |
|  | 2 | 180 | 19 | 11 | −8 | −42 |  |
|  | 3 | 130 | 15 | 9 | −6 | −40 |  |
|  | 4 | 180 | 22 | 14 | −8 | −36 |  |
|  | Mean | 157.5 ± 26.3 | 18.3 ± 3.0 | 11.0 ± 2.2 | −7.3 | −40 | 0.00063 |
| MVR blade | 1 | 180 | 20 | 14 | −6 | −30 |  |
|  | 2 | 180 | 20 | 15 | −5 | −25 |  |
|  | 3 | 150 | 18 | 12 | −6 | −33 |  |
|  | 4 | 170 | 16 | 10 | −6 | −38 |  |
|  | Mean | 170.0 ± 14.1 | 18.5 ± 1.9 | 12.8 ± 2.2 | −5.8 | −31 | 0.00018 |
| Trabectome ® | 1 | 120 | 18 | 12 | −6 | −33 |  |
|  | 2 | 130 | 21 | 12 | −9 | −43 |  |
|  | 3 | 100 | 17 | 11 | −6 | −35 |  |
|  | 4 | 120 | 19 | 10 | −9 | −47 |  |
|  | Mean | 117.5 ± 12.6 | 18.8 ± 1.7 | 11.3 ± 1.0 | −7.5 | −40 | 0.00324 |

IOP = intraocular pressure; MVR = microvitreoretinal

Histologic analysis of human cadaver eye tissue treated with the dual-blade device achieved more complete removal of TM tissue while avoiding any discernible damage to surrounding tissue. Treatment with other methods of TM removal such as MVR blade goniotomy and ab interno trabeculectomy with the Trabectome® device failed to attain equivalent histologic results to the dual-blade device. While histology data were obtained from ex vivo-treated corneal rims, similar findings were noted when treatment was performed using the ab interno approach on perfused eyes. The near-absence of TM leaflets with the dual-blade device may be beneficial in reducing the chances of future physical obstruction, and the lack of tissue damage may also reduce the inflammatory response or subsequent fibrosis at the surgical site.

In addition to potentially favorable histologic outcomes, the dual-blade device resulted in significant IOP lowering in a human eye perfusion model. Although all 3 devices yielded similar immediate reduction in IOP after use in a perfusion model, it is unclear how a more complete removal of TM tissue and decreased collateral damage with the dual-blade device of the present disclosure will translate into long term surgical outcomes when used to treat glaucoma. No correlation was found between degrees of TM treated and IOP reduction. It is plausible that IOP reduction may depend more on the number of downstream collector channels exposed rather than the absolute amount of TM removal alone.

Figure 4:
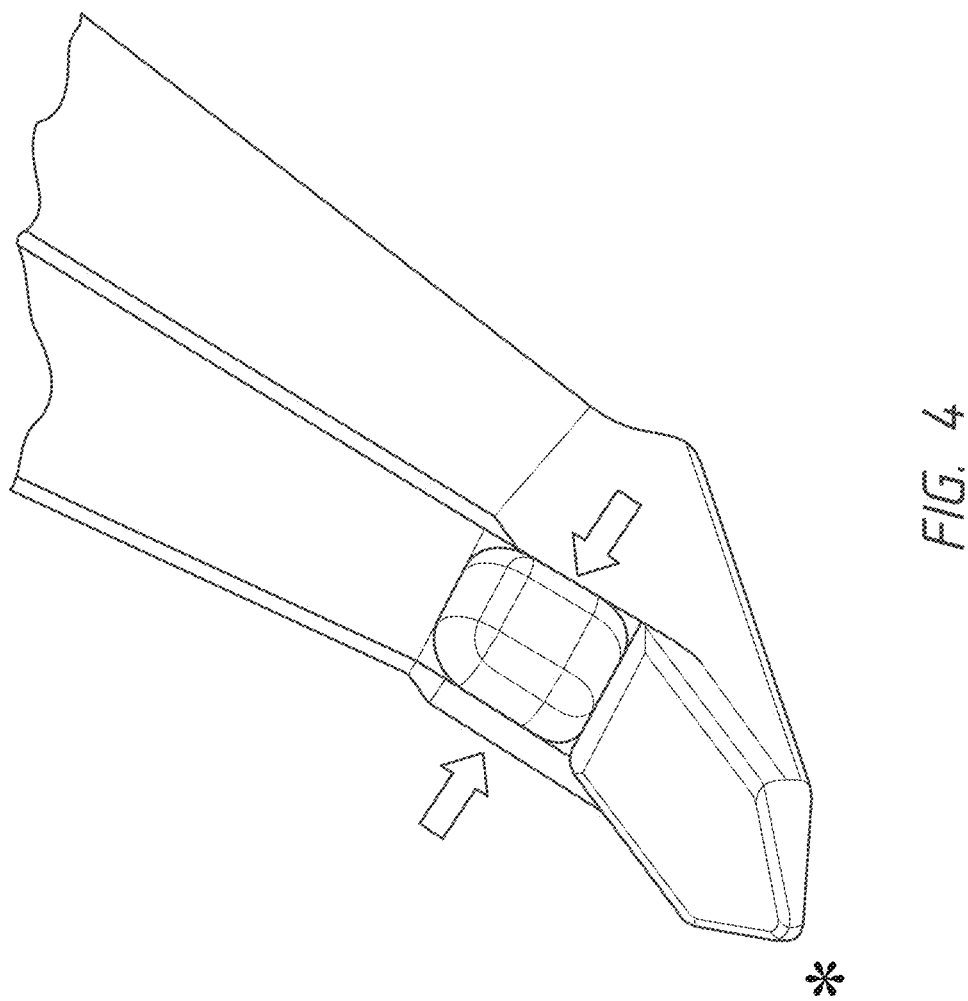
FIG. 4 shows one embodiment of the dual blade device for treatment of glaucoma. The device is illustrated to reveal the dual cutting blades (black arrows) as well as the distal point (asterisk) that is designed to pierce the trabecular meshwork ("TM") and enter into the Schlemm's canal. Once in the canal, the device is advanced so that the TM moves up the ramp from the distal point toward the dual cutting blades, which then cleanly incise the presented TM. The distance between the dual blades is designed to closely match that of the width of the TM across a range of human eyes. The inset is a photo of the first prototype device that was made of medical-grade stainless steel.
Figure 5:
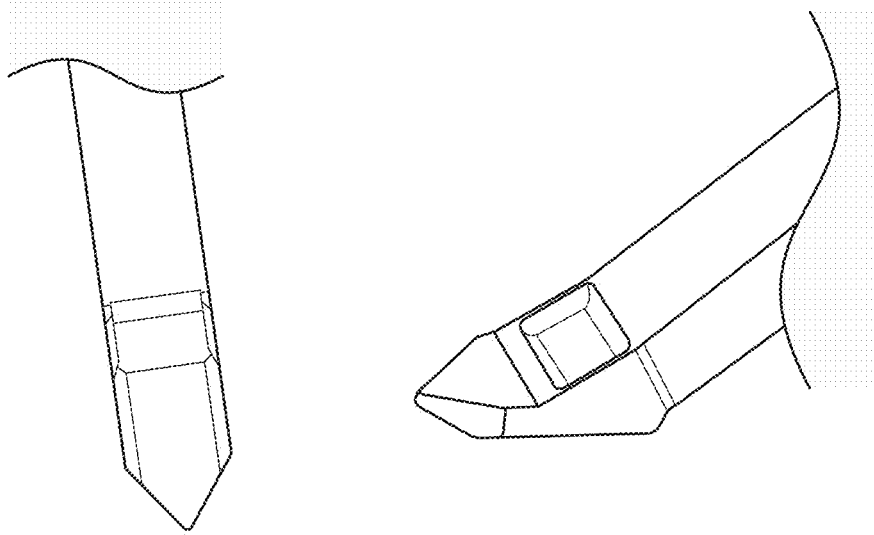
FIG. 5 shows four different angles of a fabricated embodiment of the present disclosure under 40× magnification.
Figure 5:
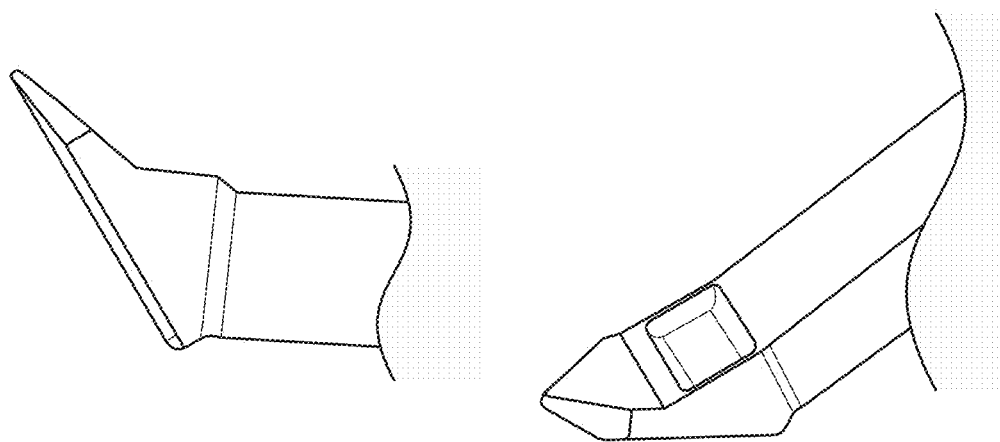
Figure 6:
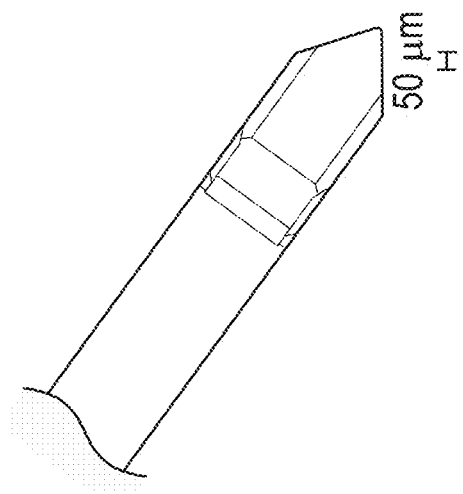
FIG. 6 shows two different angles of a fabricated embodiment of the present disclosure under 40× magnification. A size scale indicates proportions.
Figure 6:
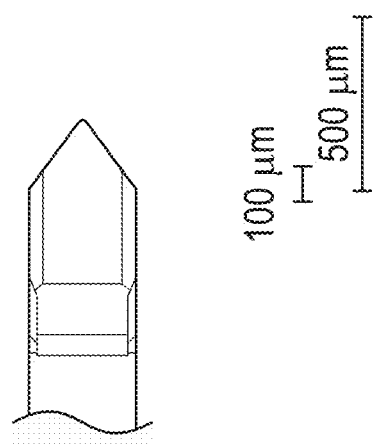
Figure 7:
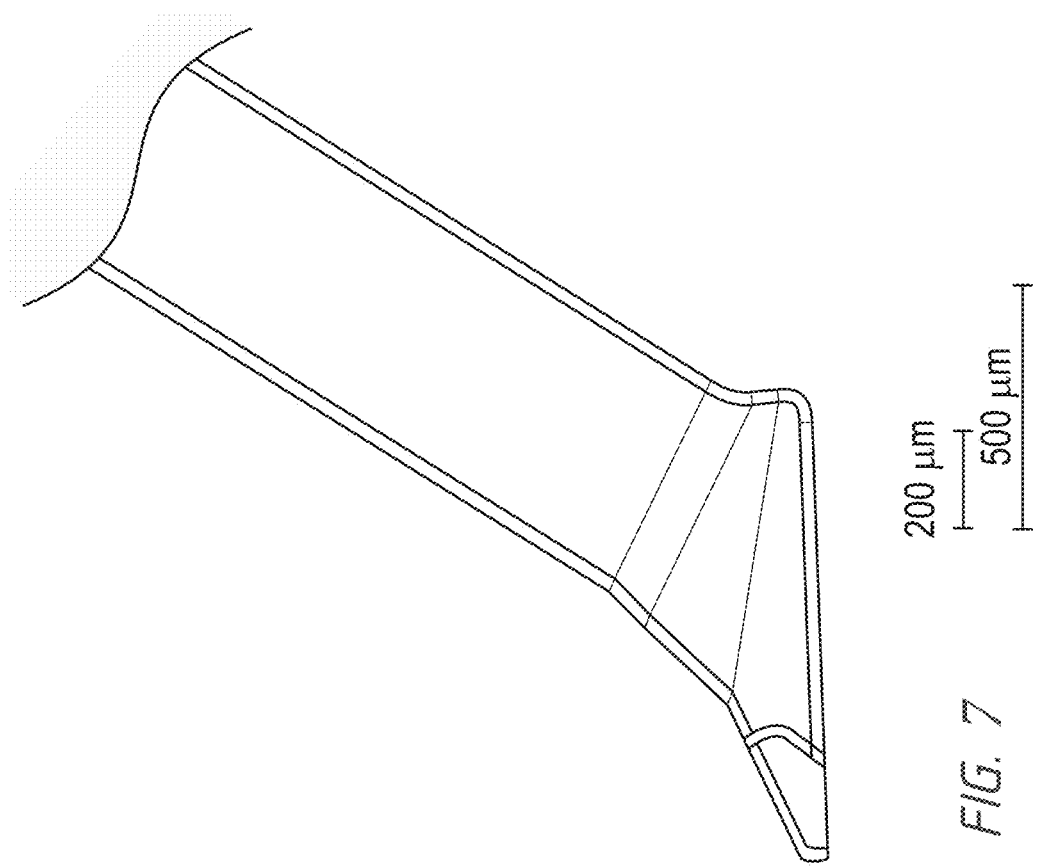
FIG. 7 shows a side angle of a fabricated embodiment of the present disclosure under 40× magnification. A size scale indicates proportions.
Figure 8:
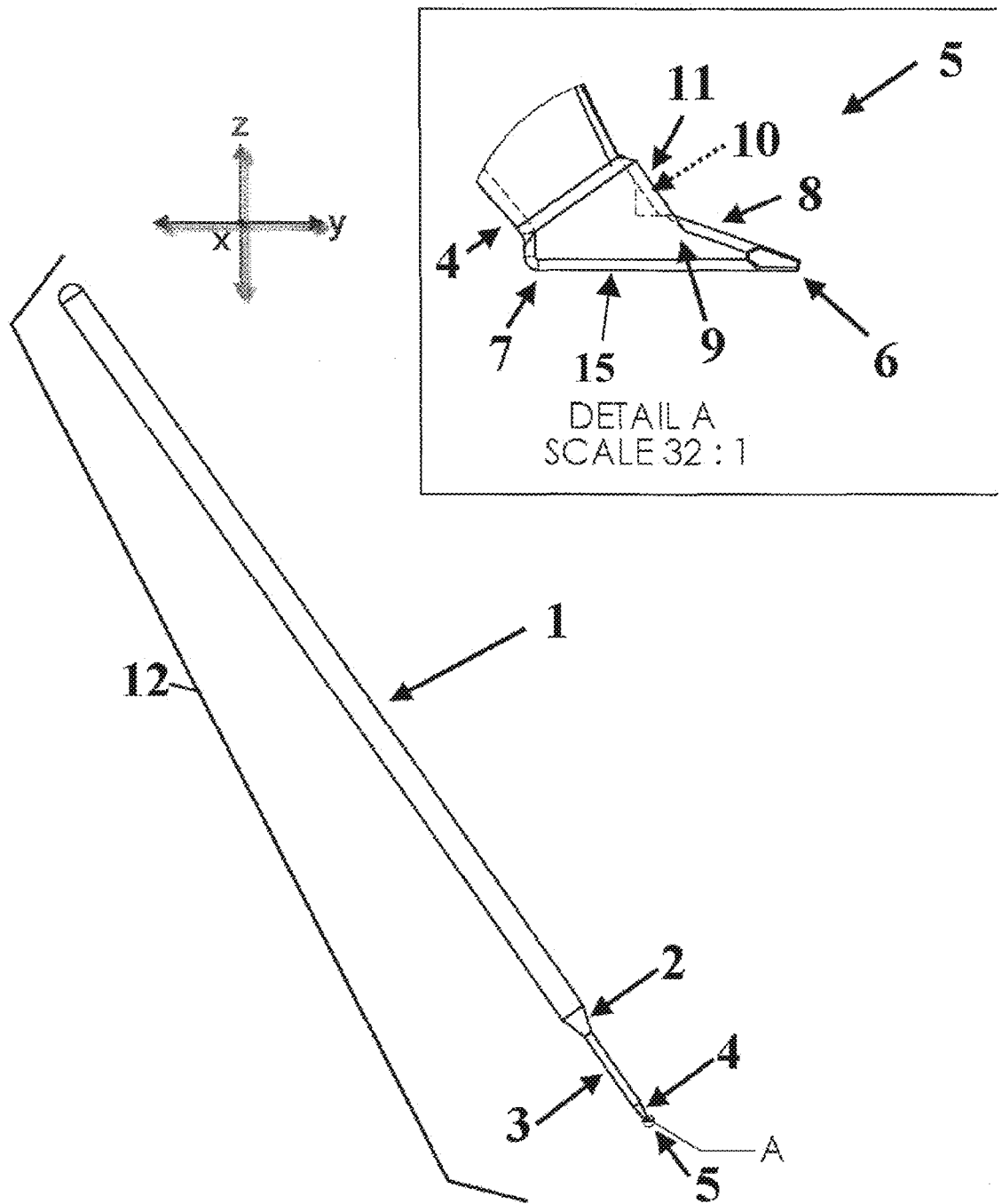
FIG. 8 shows an angled, side view of one embodiment of the device with an enlarged detailed view of the operative end of the device with the beveled platform.
Figure 9:
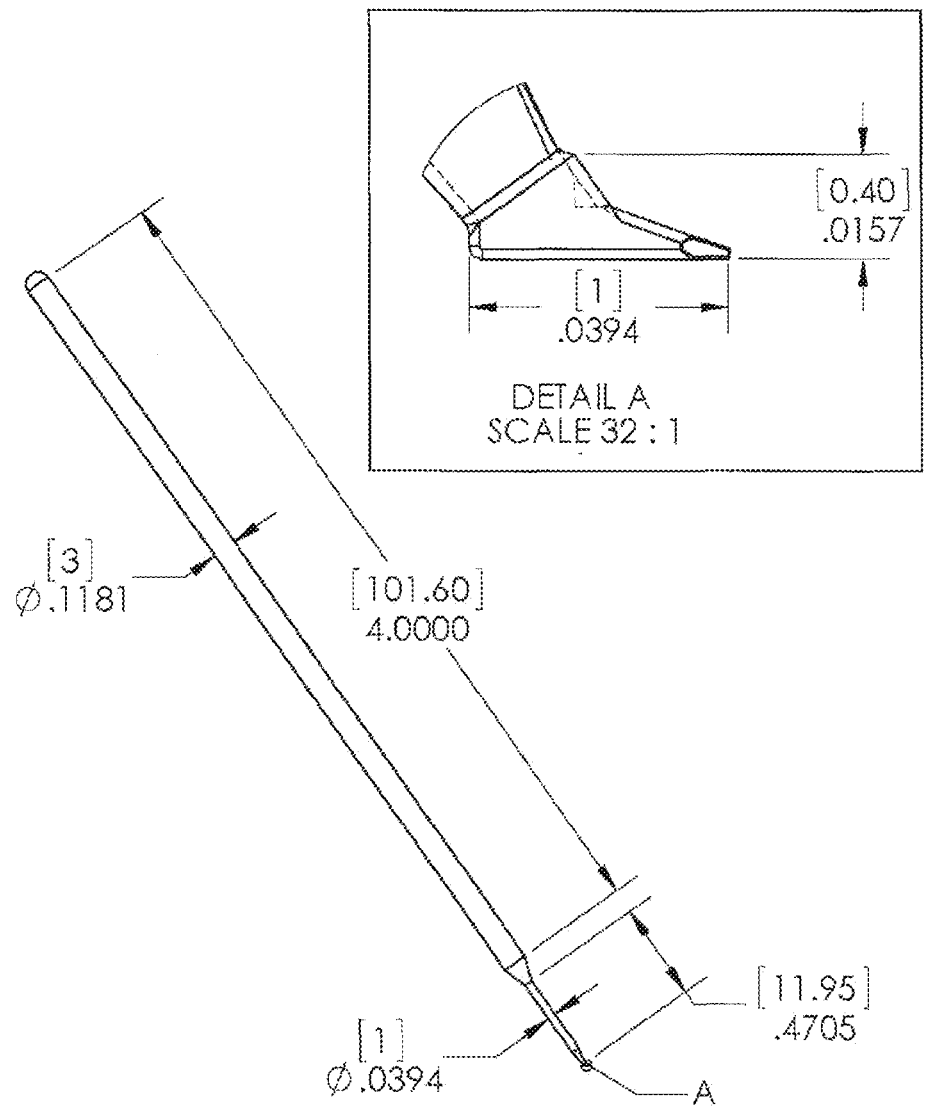
FIG. 9 shows an angled, side view of one embodiment of the device with an enlarged detailed view of the operative end of the device with the beveled platform. Measurements of specific parts are indicated.

In an effort to provide a low-cost MIGS device that can be widely used by ophthalmic surgeons, one embodiment of the present disclosure contemplates a medical-grade stainless steel dual-blade device that can successfully remove TM with no discernible collateral damage was designed. In some embodiments, the device comprises a unique dual-edge blade design using precise geometries to allow for more complete removal of TM tissue (FIG. 4). It is believed that the procedure is performed from an ab interno approach and is viscoelastic to maintain the anterior chamber. For example, the size and tip of the blade can allow for a smooth entry into the Schlemm's canal, similar to techniques used for traditional goniotomy procedures. Once in place, the tip is advanced through the Schlemm's canal and the TM is elevated along a designed ramp that guides tissue toward a set of blades positioned specifically to incise and remove TM. In contrast to the Trabectome® footplate, which is juxtaposed between the outer wall of the Schlemm's canal and the inner wall of the Schlemm's canal to provide protection during cautery, the dual-blade device transects TM and elevates TM away from the outer wall of the Schlemm's canal. It is believed that by elevating the TM along the ramp of the device as it moves forward leads to maximal tissue removal when incised by the superiorly placed and strategically angled dual blades. It is further believed that the angle between the distal cutting edge and the handle is engineered to allow maximal angle treatment through 1 incision while avoiding trauma to the cornea above or the scleral spur below. The excised TM may then be removed from the eye with forceps or aspirated during the irrigation/aspiration phase if combined with cataract extraction. In addition, the device according to embodiments of the present disclosure can easily pass through clear corneal incisions as small as 1.2 mm, thus obviating the need for additional incisions when coupled with phacoemulsification.

Another device known in the art that has been used for ab interno trabeculectomy is known as the "gonioscraper," as described by Jacobi and associates. This device consisted of a handle and curette tip and was used to remove TM by scraping the curette within the Schlemm's canal. The curette tip is in line with the handle and does not conform to the geometry of the drainage angle and adjacent structures. After promising preclinical experiments, a nonrandomized clinical trial of 25 eyes was completed. Preoperative IOP was 34.7±7.1 mm Hg on 2.2±0.56 medications and mean follow-up time was 32 months. Based on the success criteria of postoperative IOP of 19 mm Hg or less with 1 pressure-reducing agent, 15 eyes (60%) were successful. Nonetheless, complications developed in some patients including localized Descemet membrane detachments and/or anterior chamber bleeding. Histologic analysis of banked human eyes treated with the curettage showed successful removal of TM tissue, but with damage to the septa and endothelium of the external and posterior wall of the Schlemm's canal. In the data presented herein, similar damage to adjacent sclera was also observed when using the MVR blade, but was notably absent with use of one embodiment of a dual-blade device as contemplated by the present disclosure. In addition, the present disclosure contemplates a blade device geometry designed to minimize any impact to adjacent tissues such as Descemet membrane by leveraging specific angles between the handle and the distal blade as well as use of specific angles between the cutting blade and the adjacent cutting tip.

There have been reports of both success and failure with the Trabectome® device over the past few years. In a recent retrospective study of Trabectome® versus ab externo trabeculectomy, poor success rates were found in eyes treated with Trabectome® at 2 years. Of the 115 eyes treated with Trabectome®, only 22.4% achieved success with failure defined as IOP >21 mm Hg or <20% reduction in IOP. It is conceivable that, after initial opening of the canal with TM removal, the residual leaflets occlude the Schlemm's canal and/or the more distal collector channels, leading to failure of the intervention. This mechanism of failure after Trabectome® treatment would be overcome by the dual-blade device, as a more complete removal of TM tissue is produced without residual leaflets.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment"

may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A device for severing a trabecular meshwork, the device comprising:
    a shaft;
    a platform extending from the shaft, the platform comprising:
        a tip configured to pierce the trabecular meshwork;
        a bottom surface;
        a planar ramp having a single plane extending from the tip to an opposing side of the platform;
        first and second angled sides extending from the bottom surface to the planar ramp and from the tip toward the opposing side of the platform; and
        first and second lateral sides, extending above the planar ramp,
    wherein when the planar ramp is advanced between the trabecular meshwork and an outer wall of Schlemm's canal, a portion of the trabecular meshwork on the planar ramp is elevated away from the outer wall of the Schlemm's canal without cutting the portion of the trabecular meshwork from surrounding portions of the trabecular meshwork and the portion is guided to and severed by top portions of the first and second lateral sides.

2. The device of claim 1, wherein the first and second lateral sides extend upwardly at an angle toward the shaft.

3. The device of claim 1, wherein the top portions of the first and second lateral sides are linear.

4. The device of claim 1, wherein the first and second lateral sides are in perpendicular alignment to the bottom surface.

5. The device of claim 1, wherein the platform increases in thickness from the tip toward the shaft.

6. The device of claim 1, wherein the first and second lateral sides are parallel.

7. The device of claim 1, wherein the shaft is flexible.

8. The device of claim 1, wherein the top portions of the first and second lateral sides are separated by a gap.

9. The device of claim 1, wherein the first and second angled sides each form a bevel of the platform.

10. The device of claim 1, wherein the planar ramp extends at an obtuse angle from the shaft.

11. The device of claim 1, wherein a width between the first and second angled sides increases from a first width at a tip side of the platform to a second width greater than the first width at the opposing side of the platform of the platform.

12. A device for severing a trabecular meshwork, the device comprising:
    a shaft;
    a platform extending from the shaft, the platform comprising:
        a tip configured to pierce the trabecular meshwork;
        a bottom surface;
        a planar ramp having a single plane extending from the tip to an opposing side of the platform; and
        a right edge and a left edge extending towards the opposing side of the platform from the tip, the right edge and the left edge extending from the bottom surface at a height that increases between the tip and the opposing side of the platform,
    wherein when the planar ramp is advanced between the trabecular meshwork and an outer wall of Schlemm's canal, a portion of the trabecular meshwork on the planar ramp is elevated away from the outer wall of the Schlemm's canal without cutting the portion of the trabecular meshwork from surrounding portions of the trabecular meshwork and the portion of the trabecular meshwork is guided to and severed by top portions of the right and left edges.

13. The device of claim 12, wherein the right edge includes a right lateral element and the left edge includes a left lateral element.

14. The device of claim 13, wherein the right and left lateral elements are linear.

15. The device of claim 13, wherein the right and left lateral elements are parallel.

16. The device of claim 13, wherein the right and left lateral elements are separated by a recess.

17. The device of claim 13, wherein the planar ramp elevates the trabecular meshwork toward a plane extending perpendicular to the right and left lateral elements when the planar ramp is advanced between the trabecular meshwork and the outer wall of the Schlemm's canal.

18. The device of claim 12, wherein the platform increases in thickness from the tip toward the shaft.

19. The device of claim 12, wherein the shaft is flexible.

20. The device of claim 12, further comprising a gap between the right and left edges.

\* \* \* \* \*

UNITED STATES PATENT AND TRADEMARK OFFICE
CERTIFICATE OF CORRECTION

PATENT NO. : 12,213,920 B2  
APPLICATION NO. : 18/409312  
DATED : February 4, 2025  
INVENTOR(S) : Malik Y. Kahook Page 1 of 1

It is certified that error appears in the above-identified patent and that said Letters Patent is hereby corrected as shown below:

On the Title Page

In item (71) APPLICANT should read:
THE REGENTS OF THE UNIVERSITY OF COLORADO, A BODY CORPORATE In item (73) ASSIGNEE should read:
THE REGENTS OF THE UNIVERSITY OF COLORADO, A BODY CORPORATE Signed and Sealed this
Fourth Day of March, 2025

Coke Morgan Stewart
*Acting Director of the United States Patent and Trademark Office*